United States Patent
Gentile et al.

(10) Patent No.: US 7,776,904 B2
(45) Date of Patent: Aug. 17, 2010

(54) AZABICYCLO [3.1.0] HEXYLPHENYL DERIVATIVES AS MODULATORS OF DOPAMINE D3 RECEPTORS

(75) Inventors: Gabriella Gentile, Verona (IT); Dieter Hamprecht, Verona (IT); Fabrizio Micheli, Verona (IT); Adolfo Prandi, Verona (IT); Silvia Terreni, Verona (IT)

(73) Assignee: Glaxo Group Limited, Brentford, Middlesex (GB)

( * ) Notice: Subject to any disclaimer, the term of this patent is extended or adjusted under 35 U.S.C. 154(b) by 286 days.

(21) Appl. No.: 12/064,121

(22) PCT Filed: Aug. 18, 2006

(86) PCT No.: PCT/EP2006/008202

§ 371 (c)(1),
(2), (4) Date: May 9, 2008

(87) PCT Pub. No.: WO2007/022935

PCT Pub. Date: Mar. 1, 2007

(65) Prior Publication Data

US 2009/0030062 A1    Jan. 29, 2009

(30) Foreign Application Priority Data

Aug. 22, 2005 (GB) .................... 0517175.6

(51) Int. Cl.
*A61K 31/403* (2006.01)
*C07D 209/52* (2006.01)
(52) U.S. Cl. ........................ 514/412; 548/515
(58) Field of Classification Search .......... None
See application file for complete search history.

(56) References Cited

U.S. PATENT DOCUMENTS

| 4,435,419 | A | 3/1984 | Epstein et al. | |
| 6,204,284 | B1 | 3/2001 | Beer et al. | |
| 2007/0142438 | A1 | 6/2007 | Arista et al. | 514/341 |
| 2007/0249642 | A1 | 10/2007 | Bertani et al. | 514/269 |
| 2008/0058398 | A1 | 3/2008 | Anderton et al. | 514/374 |
| 2008/0167357 | A1 | 7/2008 | Hamprecht et al. | 514/384 |
| 2008/0176917 | A1 | 7/2008 | Andreotti et al. | 514/384 |
| 2008/0227837 | A1 | 9/2008 | Arista et al. | 514/384 |
| 2008/0242715 | A1 | 10/2008 | Capelli et al. | 514/384 |
| 2009/0036461 | A1 | 2/2009 | Hamprecht et al. | 514/252.06 |
| 2009/0124629 | A1 | 5/2009 | Bonanomi et al. | 514/252.06 |
| 2009/0221593 | A1 | 9/2009 | Bonanomi et al. | 514/249 |
| 2009/0221618 | A1 | 9/2009 | Arista et al. | 514/274 |

OTHER PUBLICATIONS

U.S. Appl. No. 11/917,352, filed Jun. 13, 2006, Arista, et al.
U.S. Appl. No. 12/295,024, filed Mar. 30, 2007, Bertani, et al.
U.S. Appl. No. 12/295,304, filed Mar. 30, 2007, Bertani, et al.

*Primary Examiner*—Kamal A Saeed
(74) *Attorney, Agent, or Firm*—James M. Kanagy; Edward R. Gimmi; Charles M. Kinzig

(57) ABSTRACT

The present invention relates to novel compounds of formula (IA) or a salt thereof:

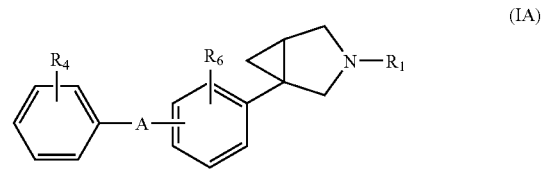

wherein:
A is attached to the phenyl group at the meta position or the para position relative to the cyclopropyl group, and is selected from the group consisting of: $-SO_2NR_5-$, $-SO_2CR_2R_3-$, $-CR_2R_3SO_2-$ and $-NR_5SO_2-$;
$R_1$ is hydrogen, $C_{1-6}$alkyl, halo$C_{1-6}$alkyl or $C_{2-6}$alkylene;
$R_2$ and $R_3$ are independently hydrogen or $C_{1-6}$alkyl;
$R_4$ is hydrogen, halogen, $C_{1-6}$alkyl, halo$C_{1-6}$alkyl, $C_{1-6}$alkoxy or halo$C_{1-6}$alkoxy;
$R_5$ is hydrogen, $C_{1-6}$alkyl, or a phenyl optionally substituted by $R_4$; and
$R_6$ is hydrogen, $C_{1-6}$alkyl, halo$C_{1-6}$alkyl, $C_{1-6}$alkoxy or halo$C_{1-6}$alkoxy;
processes for their preparation, intermediates used in these processes, pharmaceutical compositions containing them and their use in therapy, as modulators of dopamine $D_3$ receptors, e.g. to treat substance related disorders, as antipsychotic agents premature ejaculation or cognition impairment.

10 Claims, No Drawings

AZABICYCLO [3.1.0] HEXYLPHENYL DERIVATIVES AS MODULATORS OF DOPAMINE D3 RECEPTORS

The present invention relates to novel compounds, processes for their preparation, intermediates used in these processes, pharmaceutical compositions containing them and their use in therapy, as modulators of dopamine $D_3$ receptors.

WO 2002/40471 (SmithKline Beecham) discloses certain benzazepine compounds having activity at the dopamine $D_3$ receptor.

A new class of compounds which have affinity for dopamine receptors, in particular the dopamine $D_3$ receptor has been found. These compounds have potential in the treatment of conditions wherein modulation, especially antagonism/inhibition, of the $D_3$ receptor is beneficial, e.g. to treat drug dependency or as antipsychotic agents.

The present invention provides a compound of formula (I) or a salt thereof:

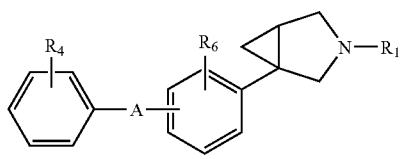

(I)

wherein:

A is attached to the phenyl group at the meta position or the para position relative to the cyclopropyl group, and is selected from the group consisting of: —S—, —SO—, —SO$_2$—, —SCR$_2$R$_3$—, —SO$_2$NR$_5$—, SO$_2$CR$_2$R$_3$—, —SOCR$_2$R$_3$— and —NR$_5$SO$_2$—;

R$_1$ is hydrogen, C$_{1-6}$alkyl, haloC$_{1-6}$alkyl or C$_{2-6}$alkylene;

R$_2$ and R$_3$ are independently hydrogen or C$_{1-6}$alkyl;

R$_4$ is hydrogen, C$_{1-6}$alkyl, haloC$_{1-6}$alkyl, C$_{1-6}$alkoxy or haloC$_{1-6}$alkoxy;

R$_5$ is hydrogen, C$_{1-6}$alkyl, or a phenyl optionally substituted by R$_4$; and R$_6$ is hydrogen, C$_{1-6}$alkyl, haloC$_{1-6}$alkyl, C$_{1-6}$alkoxy or haloC$_{1-6}$alkoxy.

In another embodiment the present invention provides a compound of formula (IA) or a salt thereof:

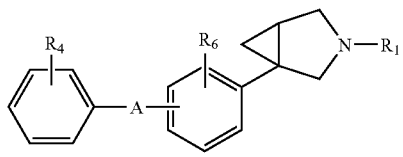

(IA)

wherein:

A is attached to the phenyl group at the meta position or the para position relative to the cyclopropyl group, and is selected from the group consisting of: —SO$_2$NR$_5$—, —SO$_2$CR$_2$R$_3$—, —CR$_2$R$_3$SO$_2$— and —NR$_5$SO$_2$—;

R$_1$ is hydrogen, C$_{1-6}$alkyl, haloC$_{1-6}$alkyl or C$_{2-6}$alkylene;

R$_2$ and R$_3$ are independently hydrogen or C$_{1-6}$alkyl;

R$_4$ is hydrogen, halogen, C$_{1-6}$alkyl, haloC$_{1-6}$alkyl, C$_{1-6}$alkoxy or haloC$_{1-6}$alkoxy;

R$_5$ is hydrogen, C$_{1-6}$alkyl, or a phenyl optionally substituted by R$_4$; and R$_6$ is hydrogen, C$_{1-6}$alkyl, haloC$_{1-6}$alkyl, C$_{1-6}$alkoxy or haloC$_{1-6}$alkoxy.

In a further embodiment, the present invention provides a compound of formula (IB) or a salt thereof:

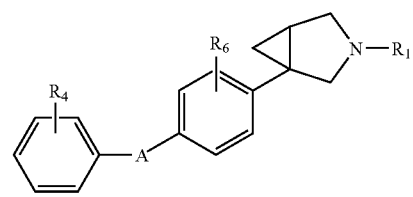

(IB)

wherein:

A is selected from the group consisting of: —SO$_2$NR$_5$—, —SO$_2$CR$_2$R$_3$— and —NR$_5$SO$_2$—;

R$_1$ is hydrogen, C$_{1-6}$alkyl, haloC$_{1-6}$alkyl or C$_{2-6}$alkylene;

R$_2$ and R$_3$ are independently hydrogen or C$_{1-6}$alkyl;

R$_4$ is hydrogen, halogen, C$_{1-6}$alkyl, haloC$_{1-6}$alkyl, C$_{1-6}$alkoxy or haloC$_{1-6}$alkoxy;

R$_5$ is hydrogen, C$_{1-6}$alkyl, or a phenyl optionally substituted by R$_4$; and R$_6$ is hydrogen, C$_{1-6}$alkyl, haloC$_{1-6}$alkyl, C$_{1-6}$alkoxy or haloC$_{1-6}$alkoxy.

In a further embodiment, the present invention provides a compound of formula (IC) or a salt thereof:

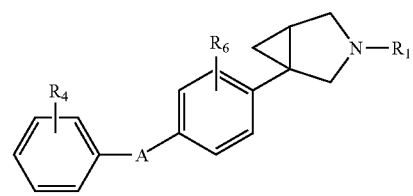

(IC)

wherein:

A is selected from the group consisting of: —SO$_2$NR$_5$—, —SO$_2$CR$_2$R$_3$— and —NR$_5$SO$_2$—;

R$_1$ is hydrogen, C$_{1-6}$alkyl, haloC$_{1-6}$alkyl or C$_{2-6}$alkylene;

R$_2$ and R$_3$ are independently hydrogen or C$_{1-6}$alkyl;

R$_4$ is hydrogen, halogen, C$_{1-6}$alkyl, haloC$_{1-6}$alkyl, C$_{1-6}$alkoxy or haloC$_{1-6}$alkoxy;

R$_5$ is hydrogen; and

R$_6$ is hydrogen, C$_{1-6}$alkyl, haloC$_{1-6}$alkyl, C$_{1-6}$alkoxy or haloC$_{1-6}$alkoxy.

In a still further embodiment, the present invention provides a compound of formula (ID) or a salt thereof:

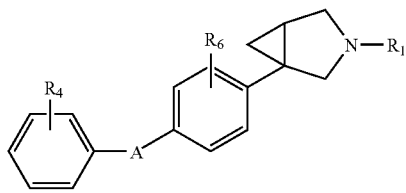

(ID)

wherein:

A is —CR$_2$R$_3$SO$_2$—;

R$_1$ is hydrogen, C$_{1-6}$alkyl, haloC$_{1-6}$alkyl or C$_{2-6}$alkylene;

R$_2$ and R$_3$ are independently hydrogen or C$_{1-6}$alkyl;

R$_4$ is hydrogen, halogen, C$_{1-6}$alkyl, halogen or C$_{1-6}$alkoxy;

R$_5$ is hydrogen, C$_{1-6}$alkyl, or a phenyl optionally substituted by R$_4$; and R$_6$ is hydrogen, C$_{1-6}$alkyl, haloC$_{1-6}$alkyl, C$_{1-6}$alkoxy or haloC$_{1-6}$alkoxy.

In another embodiment, the present invention provides a compound of formula (IE) or a salt thereof:

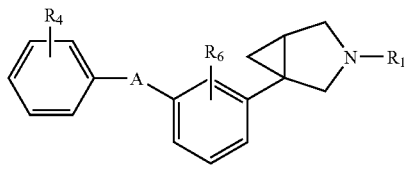

(IE)

wherein:

A is selected from the group consisting of: —SCR$_2$R$_3$—, —SO$_2$NR$_5$—, SO$_2$CR$_2$R$_3$—, CR$_2$R$_3$SO$_2$—; and —NR$_5$SO$_2$—;

R$_1$ is C$_{1-6}$alkyl, haloC$_{1-6}$alkyl or C$_{2-6}$alkylene;

R$_2$ and R$_3$ are independently hydrogen or C$_{1-6}$alkyl;

R$_4$ is hydrogen, halogen, C$_{1-6}$alkyl, haloC$_{1-6}$alkyl, C$_{1-6}$alkoxy or haloC$_{1-6}$alkoxy;

R$_5$ is hydrogen, C$_{1-6}$alkyl, or a phenyl optionally substituted by R$_4$; and R$_6$ is hydrogen, C$_{1-6}$alkyl, haloC$_{1-6}$alkyl, C$_{1-6}$alkoxy or haloC$_{1-6}$alkoxy.

The term "C$_{1-6}$alkyl" as used herein as a group or a part of the group refers to a linear or branched saturated hydrocarbon group containing from 1 to 6 carbon atoms. Examples of such groups include methyl, ethyl, n-propyl, isopropyl, n-butyl, isobutyl, sec-butyl, tert butyl, n-pentyl, isopentyl, neopentyl or hexyl and the like.

The term "C$_{2-6}$alkylene" as used herein refers to a linear or branched hydrocarbon group containing one or more carbon-carbon double bonds and having from 2 to 6 carbon atoms. Examples of such groups include ethenyl, propenyl, butenyl, pentenyl or hexenyl and the like.

The term "C$_{1-6}$alkoxy" as used herein refers to an —O—C$_{1-6}$alkyl group wherein C$_{1-6}$alkyl is as defined herein. Examples of such groups include methoxy, ethoxy, propoxy, butoxy, pentoxy or hexoxy and the like.

The term "halogen" and its abbreviation "halo" refer to fluorine (F), chlorine (Cl), bromine (Br) or iodine (I). Where the term "halo" is used before another group, it indicates that the group is substituted by one, two or three halogen atoms. For example, "haloC$_{1-6}$alkyl" refers to groups such as trifluoromethyl, bromoethyl, trifluoropropyl, and other groups derived from C$_{1-6}$alkyl groups as defined above; and the term "haloC$_{1-6}$alkoxy" refers to groups such as trifluoromethoxy, bromoethoxy, trifluoropropoxy, and other groups derived from C$_{1-6}$alkoxy groups as defined above.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumaine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

In one embodiment, R$_4$ is C$_{1-6}$alkyl such as isopropyl.

In another embodiment, R$_4$ is haloC$_{1-6}$alkyl (such as —CF$_3$).

In a further embodiment, R$_4$ is halogen (such as iodine).

In one embodiment, A is —SO$_2$NR$_5$— wherein R$_5$ is hydrogen or methyl, or A is —SO$_2$CR$_2$R$_3$— wherein R$_2$ and R$_3$ are hydrogen.

In a further embodiment, A is —SO$_2$NR$_5$— wherein R$_5$ is hydrogen.

In another embodiment, A is —CR$_2$R$_3$SO$_2$— wherein R$_2$ and R$_3$ are hydrogen.

In one embodiment, R$_1$ is hydrogen, C$_{1-2}$alkyl or C$_{2-4}$alkylene.

In another embodiment, R$_1$ is haloC$_{1-6}$alkyl.

In one embodiment, R$_6$ is hydrogen or C$_{1-2}$alkoxy.

It will be appreciated that compounds of formula (I) possess at least two chiral centres, namely at position 1 and 5 in the 3-azabicyclo[3.1.0]hexane portion of the molecule. Because of the presence of the fused cyclopropane compounds of formula (I) are believed to have a "cis" disposition of the substituents (both groups linked to the bicyclic ring system are on the same face of this bicyclic ring system). Thus, the compounds may exist in two stereoisomers which are enantiomers with respect to the chiral centres in the cyclopropane. It will also be appreciated, in common with most biologically active molecules that the level of biological activity may vary between the individual stereoisomers of a given molecule. It is intended that the scope of the invention includes all individual stereoisomers (diastereoisomers and enantiomers) and all mixtures thereof, including but not limited to racemic mixtures, which demonstrate appropriate biological activity with reference to the procedures described herein.

In another embodiment of the present invention compounds of formula (I)' are provided which correspond to the compounds of formula (I) having "cis" disposition, represented by the bold highlight of the two bonds near the cyclopropyl moiety:

(I)' wherein $R_4$, $R_1$ and A are defined as above for compounds of formula (I).

In compounds of formula (I)' there are at least two chiral centres, which are located in the cyclopropane portion, as depicted below (the bold highlight of the bonds means the "cis" configuration):

(I)'

↓ Resolution (1R,5S)

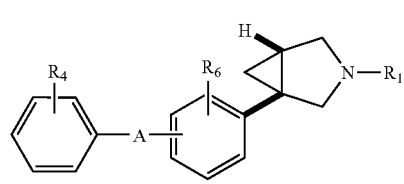

(1S,5R)

In a further embodiment of the present invention, there is provided a compound of formula (Ia) or a salt thereof that correspond to a stereochemical isomer of a compound of formula (I), enriched in configuration (1S,5R):

(Ia)

wherein $R_1$, $R_4$, $R_6$ and A are defined as above for compounds of formula (I).

In a further embodiment of the present invention, there is provided a compound of formula (Ib) or a salt thereof that correspond to a stereochemical isomer of a compound of formula (I), enriched in configuration (1R,5S):

(Ib)

wherein $R_1$, $R_4$, $R_6$ and A are defined as above for compounds of formula (I).

In another embodiment of the present invention compounds of formula (IA)' are provided which correspond to the compounds of formula (IA) having "cis" disposition, represented by the bold highlight of the two bonds near the cyclopropyl moiety:

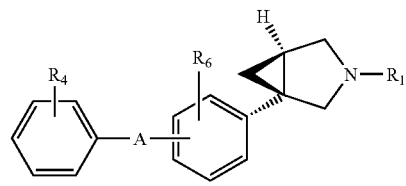

wherein $R_4$, $R_1$ and A are defined as above for compounds of formula (IA).

In compounds of formula (IA)' there are at least two chiral centres, which are located in the cyclopropane portion, as depicted below (the bold highlight of the bonds means the "cis" configuration):

(IA)'

↓ Resolution

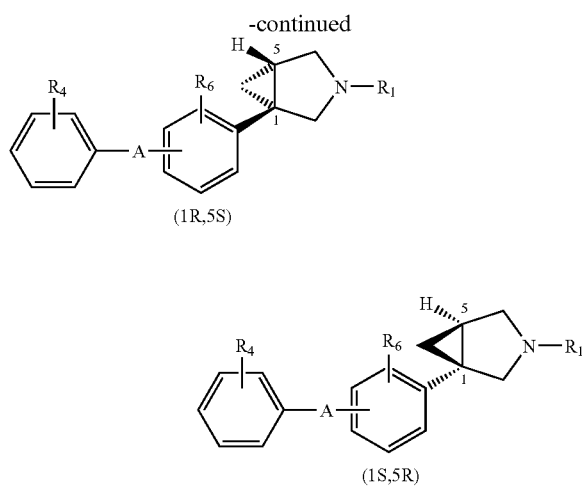

In a further embodiment of the present invention, there is provided a compound of formula (IAa) or a salt thereof that correspond to a stereochemical isomer of a compound of formula (IA), enriched in configuration (1S,5R):

(IAa)

wherein $R_1$, $R_4$, $R_6$ and A are defined as above for compounds of formula (IA).

In a further embodiment of the present invention, there is provided a compound of formula (IAb) or a salt thereof that correspond to a stereochemical isomer of a compound of formula (IA), enriched in configuration (1R,5S):

(IAb)

wherein $R_1$, $R_4$, $R_6$ and A are defined as above for compounds of formula (IA).

In another embodiment of the present invention compounds of formula (IB)' are provided which correspond to the compounds of formula (IB) having "cis" disposition, represented by the bold highlight of the two bonds near the cyclopropyl moiety:

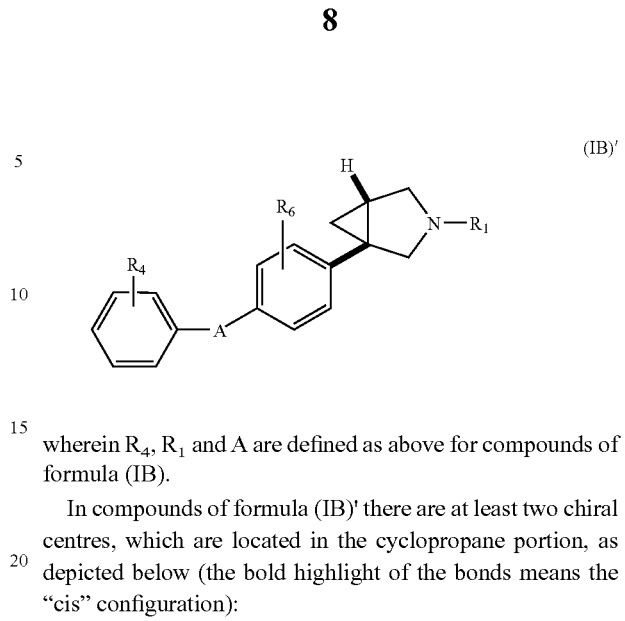

wherein $R_4$, $R_1$ and A are defined as above for compounds of formula (IB).

In compounds of formula (IB)' there are at least two chiral centres, which are located in the cyclopropane portion, as depicted below (the bold highlight of the bonds means the "cis" configuration):

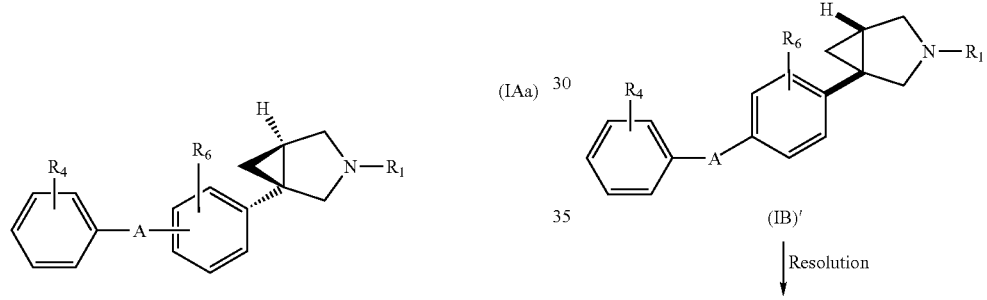

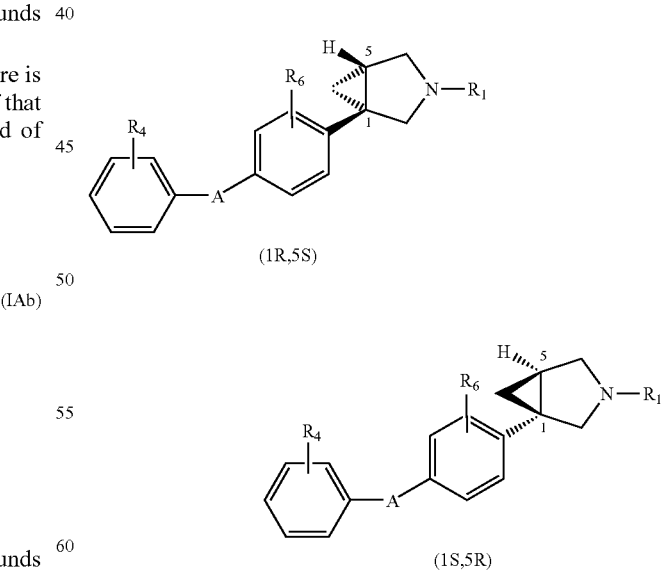

In a further embodiment of the present invention, there is provided a compound of formula (IBa) or a salt thereof that correspond to a stereochemical isomer of a compound of formula (IB), enriched in configuration (1S,5R):

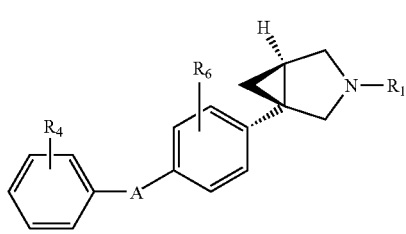

(IBa)

wherein $R_1$, $R_4$, $R_6$ and A are defined as above for compounds of formula (IB).

In a further embodiment of the present invention, there is provided a compound of formula (IBb) or a salt thereof that correspond to a stereochemical isomer of a compound of formula (IB), enriched in configuration (1R,5S):

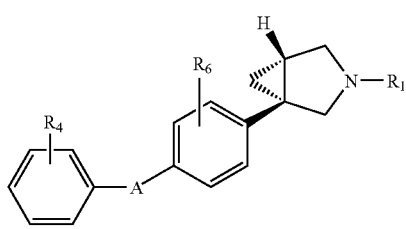

(IBb)

wherein $R_1$, $R_4$, $R_6$ and A are defined as above for compounds of formula (IB).

In another embodiment of the present invention compounds of formula (IC)' are provided which correspond to the compounds of formula (IC) having "cis" disposition, represented by the bold highlight of the two bonds near the cyclopropyl moiety:

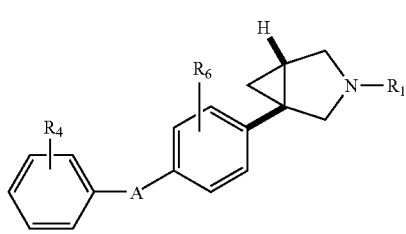

(IC)' wherein $R_4$, $R_1$ and A are defined as above for compounds of formula (IC).

In compounds of formula (IC)' there are at least two chiral centres, which are located in the cyclopropane portion, as depicted below (the bold highlight of the bonds means the "cis" configuration):

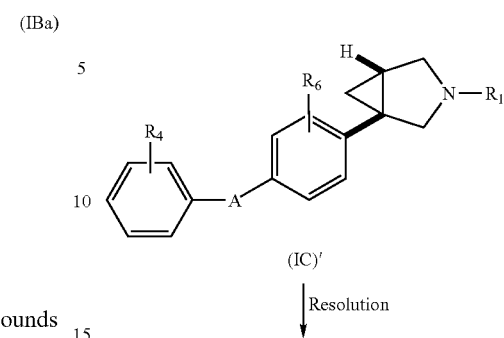

(IC)'

↓ Resolution

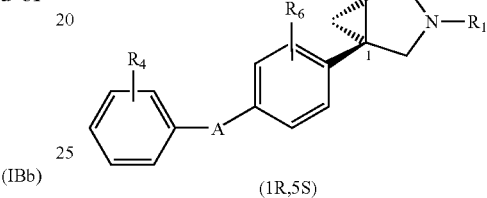

(1R,5S)

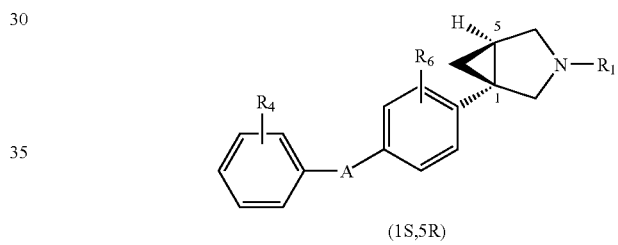

(1S,5R)

In a further embodiment of the present invention, there is provided a compound of formula (ICa) or a salt thereof that correspond to a stereochemical isomer of a compound of formula (IC), enriched in configuration (1S,5R):

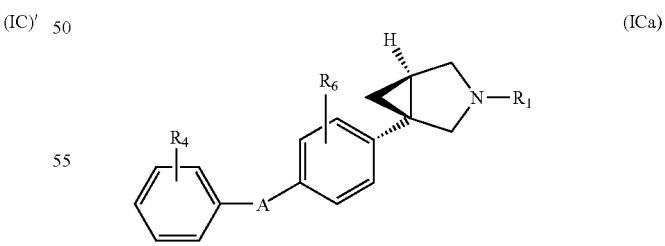

(ICa)

wherein $R_1$, $R_4$, $R_6$ and A are defined as above for compounds of formula (IC).

In a further embodiment of the present invention, there is provided a compound of formula (ICb) or a salt thereof that correspond to a stereochemical isomer of a compound of formula (IC), enriched in configuration (1R,5S):

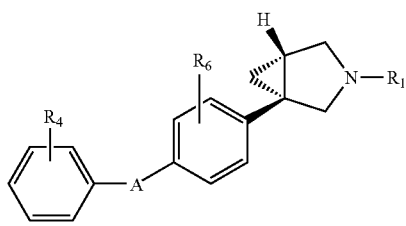

(ICb)

wherein $R_1$, $R_4$, $R_6$ and A are defined as above for compounds of formula (IC).

In another embodiment of the present invention compounds of formula (ID)' are provided which correspond to the compounds of formula (ID) having "cis" disposition, represented by the bold highlight of the two bonds near the cyclopropyl moiety:

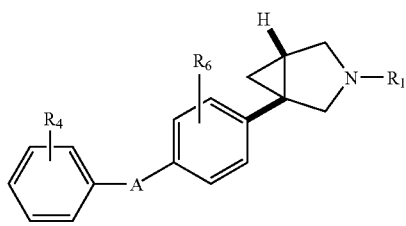

(ID)' wherein $R_4$, $R_1$ and A are defined as above for compounds of formula (ID).

In compounds of formula (ID)' there are at least two chiral centres, which are located in the cyclopropane portion, as depicted below (the bold highlight of the bonds means the "cis" configuration):

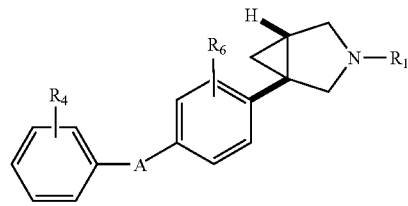

(ID)'

↓ Resolution

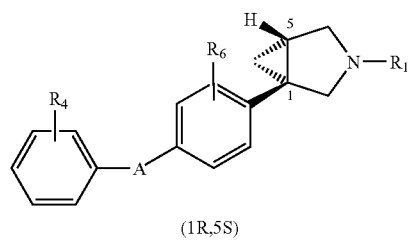

(1R,5S)

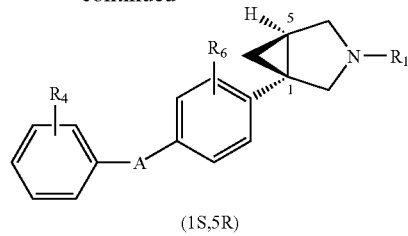

(1S,5R)

In a further embodiment of the present invention, there is provided a compound of formula (IDa) or a salt thereof that correspond to a stereochemical isomer of a compound of formula (ID), enriched in configuration (1S,5R):

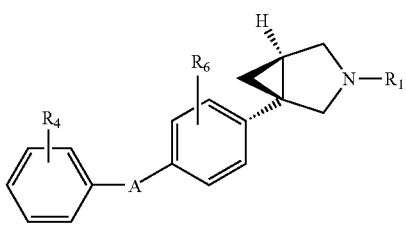

(IDa)

wherein $R_1$, $R_4$, $R_6$ and A are defined as above for compounds of formula (ID).

In a further embodiment of the present invention, there is provided a compound of formula (IDb) or a salt thereof that correspond to a stereochemical isomer of a compound of formula (ID), enriched in configuration (1R,5S):

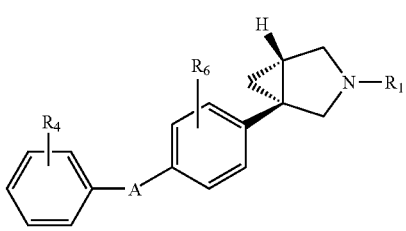

(IDb)

wherein $R_1$, $R_4$, $R_6$ and A are defined as above for compounds of formula (ID).

In another embodiment of the present invention compounds of formula (IE)' are provided which correspond to the compounds of formula (IE) having "cis" disposition, represented by the bold highlight of the two bonds near the cyclopropyl moiety:

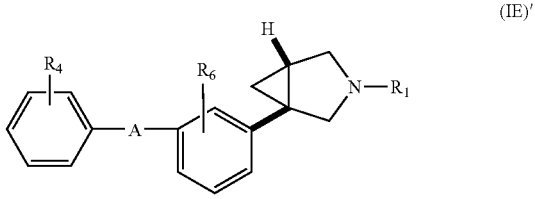

(IE)' wherein R₄, R₁ and A are defined as above for compounds of formula (IE).

In compounds of formula (IE)' there are at least two chiral centres, which are located in the cyclopropane portion, as depicted below (the bold highlight of the bonds means the "cis" configuration):

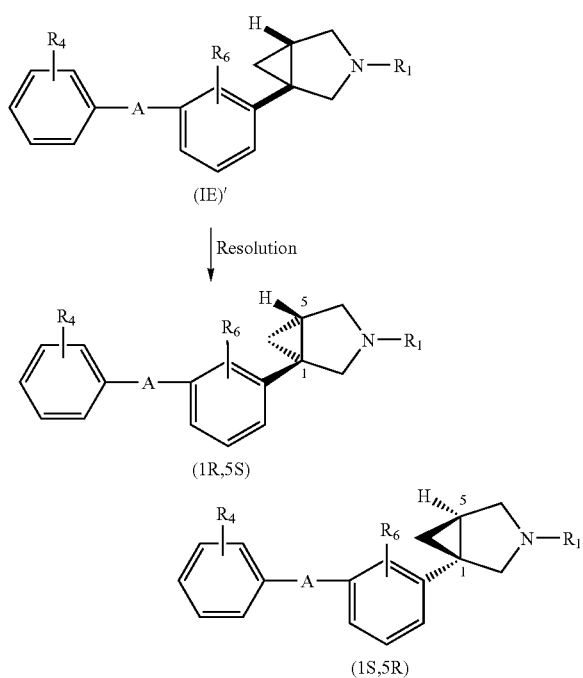

In a further embodiment of the present invention, there is provided a compound of formula (IEa) or a salt thereof that correspond to a stereochemical isomer of a compound of formula (IE), enriched in configuration (1S,5R):

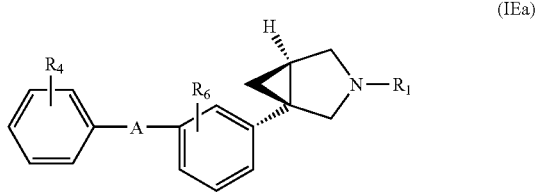

wherein R₁, R₄, R₆ and A are defined as above for compounds of formula (IE).

In a further embodiment of the present invention, there is provided a compound of formula (IEb) or a salt thereof that correspond to a stereochemical isomer of a compound of formula (IE), enriched in configuration (1R,5S):

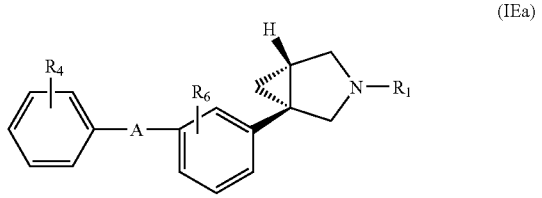

wherein R₁, R₄, R₆ and A are defined as above for compounds of formula (IE).

Example compounds of the present invention include:
N-{4-[(1S,5R/1R,5S)-3-azabicyclo[3.1.0]hex-1-yl]phenyl}-4-(1-methylethyl)benzenesulfonamide;
N-{4-[(1R,5S or 1S,5R)-3-azabicyclo[3.1.0]hex-1-yl]phenyl}-4-(1-methylethyl)benzenesulfonamide);
4-(1-methylethyl)-N-{4-[(1S,5R/1R,5S)-3-(2-propen-1-yl)-3-azabicyclo[3.1.0]hex-1-yl]phenyl}benzenesulfonamide;
N-{4-[(1S,5R/1R,5S)-3-Ethyl-3-azabicyclo[3.1.0]hex-1-yl]phenyl}-4-(1-methylethyl)benzenesulfonamide;
N-{4-[(1S,5R/1R,5S)-3-Methyl-3-azabicyclo[3.1.0]hex-1-yl]phenyl}-4-(1-methylethyl)benzenesulfonamide;
N-{3-[(1S,5R/1R,5S))-3-methyl-3-azabicyclo[3.1.0]hex-1-yl]phenyl}-4-(1-methylethyl)benzenesulfonamide;
N-{4-[(1S,5R/1R,5S)-3-azabicyclo[3.1.0]hex-1-yl]phenyl}-N-methyl-4-(1-methylethyl)benzenesulfonamide;
N-[4-[(1S,5R/1R,5S)-3-Azabicyclo[3.1.0]hex-1-yl]-2-(methyloxy)phenyl]-4-(1-methylethyl)benzenesulfonamide;
(1S,5R/1R,5S)-1-[4-({[4-(1-Methylethyl)phenyl]sulfonyl}methyl)phenyl]-3-azabicyclo[3.1.0]hexane;
N-{4-[(1S,5R/1R,5S)-3-Azabicyclo[3.1.0]hex-1-yl]phenyl}-4-(trifluoromethyl)benzenesulfonamide;
N-{4-[(1S,5R/1R,5S)-3-azabicyclo[3.1.0]hex-1-yl]phenyl}-4-iodobenzenesulfonamide;
N-{4-[(1S,5R/1R,5S)-3-azabicyclo[3.1.0]hex-1-yl]phenyl}-4-butylbenzenesulfonamide;
N-{4-[(1S,5R/1R,5S)-3-azabicyclo[3.1.0]hex-1-yl]phenyl}-4-(1,1-dimethylpropyl)benzenesulfonamide;
N-{4-[(1S,5R/1R,5S)-3-azabicyclo[3.1.0]hex-1-yl]phenyl}-4-[(trifluoromethyl)oxy]benzenesulfonamide;
N-{4(1S,5R/1R,5S)-)-3-(3-fluoropropyl)-3-azabicyclo[3.1.0]hex-1-yl]phenyl}-4-(1-methylethyl)benzenesulfonamide;
(1R,5S/1S, 5R)-1-[4-({[4-(1-methylethyl)phenyl]methyl}sulfonyl)phenyl]-3-azabicyclo[3.1.0]hexane;
(1R,5S/1S,5R)-3-(3-fluoropropyl)-1-[4-({[4-(1-methylethyl)phenyl]methyl}sulfonyl)phenyl]-3-azabicyclo[3.1.0]hexane;
and salts thereof.

It will be appreciated that for use in medicine the salts of the compounds of the invention should be pharmaceutically (i.e physiologically) acceptable. Suitable pharmaceutically acceptable salts will be apparent to those skilled in the art and include for example acid addition salts formed with inorganic acids e.g. hydrochloric, hydrobromic, sulfuric, nitric or phosphoric acid; and organic acids e.g. succinic, maleic, acetic, fumaric, citric, tartaric, benzoic, p-toluenesulfonic, methanesulfonic or naphthalenesulfonic acid. Other non-pharmaceutically acceptable salts eg. oxalates, may be used, for example in the isolation of compounds of the invention and are included within the scope of this invention. Also included within the scope of the invention are solvates, hydrates, complexes and prodrugs of compounds of the invention. Pharmaceutical acceptable salts may also be prepared from other salts, including other salts, of the compound of formula (I) using conventional methods.

Certain of the compounds of the invention may form acid addition salts with one or more equivalents of the acid. The present invention includes within its scope all possible stoichiometric and non-stoichiometric forms. Certain of the compounds of the invention may form acid addition salts with less than one equivalent of the acid, or one or more equivalents of the acid. The present invention includes within its scope all possible stoichiometric and non-stoichiometric forms.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference. Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alky silyl groups, such as trimethylsilyl or tert-butyldimethylsilyl; alkyl ethers such as tetrahydropyranyl or tert-butyl; or esters such as acetate.

When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure.

The present invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$. Compounds of the present invention and salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

In one embodiment of the present invention compounds are provided having a molecular weight of 800 or less. In another embodiment compounds are provided having a molecular weight of 600 or less. Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

The present invention also provides a process for preparing a compound of formula (I) or a salt thereof as defined above, the process comprising:

(a) reacting a compound of formula (II):

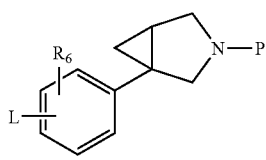
(II)

wherein P may be a suitable protecting group or a substituent $R_1$ as defined for formula (I) and L is a leaving group, with a compound of formula (III):

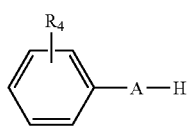
(III)

wherein $R_4$ and A are as defined for formula (I); or (b) for a compound of formula (Ia), i.e. a compound of formula (I) wherein A is —$SO_2NH$—, reacting a compound of formula (IV):

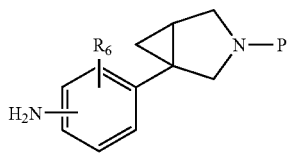
(IV)

wherein P may be a suitable protecting group or a substituent $R_1$ as defined for formula (I) and $R_6$ is as defined for formula (I) with a compound of formula (V):

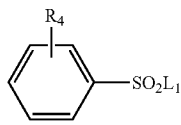
(V)

wherein $R_4$ is as defined for formula (I) and $L_1$ is a leaving group; or (c) for a compound of formula (Ib), i.e. a compound of formula (I) wherein A is —$SO_2CR_2R_3$—, reacting a compound of formula (VI):

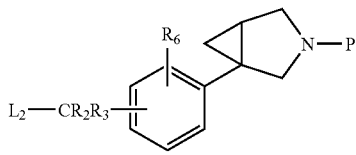
(VI)

wherein P may be a suitable protecting group or a substituent $R_1$ as defined for formula (I), $R_2$, $R_3$, and $R_6$ are as defined for formula (I) and $L_2$ is a leaving group, with a compound of formula (VII) (step I):

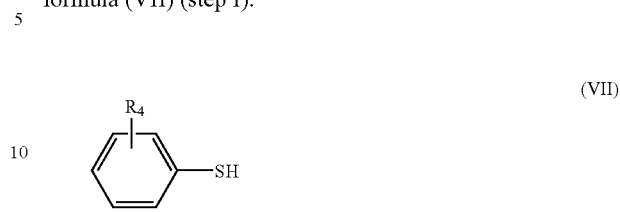
(VII)

wherein $R_4$ is as defined for formula (I), followed by an oxidation step for the sulphur atom (step II);

(d) for a compound of formula (Ic), i.e. a compound of formula (I) wherein A is —$NR_5SO_2$—, reacting a compound of formula (VIII):

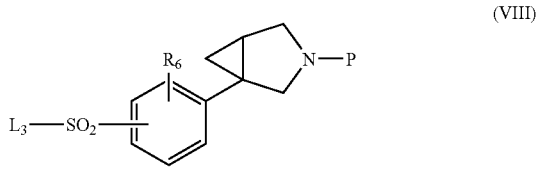
(VIII)

wherein P may be a suitable protecting group or a substituent $R_1$ as defined for formula (I) and $R_6$ is as defined for formula (I) and $L_3$ is a leaving group, with a compound of formula (IX):

(IX)

wherein $R_4$ is as defined for formula (I);

(e) for a compound of formula (Id), i.e. a compound of formula (I) wherein $R_1$ is not hydrogen, reacting a compound of formula (Ie), i.e. a compound of formula (I) wherein $R_1$ is hydrogen:

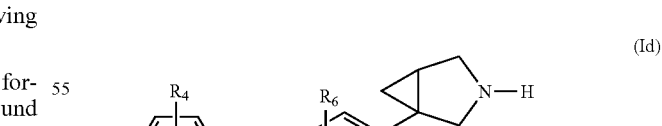
(Id)

with a compound $R_1L_4$ of formula, wherein R1 is as defined for formula (I) and $L_4$ is a leaving group;

(f) for a compound of formula (Ie), i.e. a compound of formula (I) wherein A is —$CR_2R_3SO_2$—, reacting a compound of formula (II):

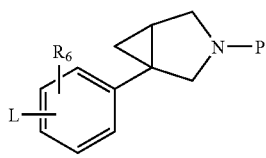

as above defined, with a compound of formula (X) (step I):

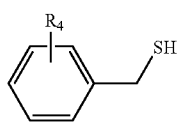

wherein $R_4$ is as defined for formula (I), followed by an oxidation step for the sulphur atom (step II);

and thereafter optionally for process (a), (b), (c), (d), (e) or (f):

(i) removing any protecting group(s); and/or (ii) forming a salt; and/or (iii) converting a compound of formula (I) or a salt thereof to another compound of formula (I) or a salt thereof.

In process (a) L is a leaving group such as halogen, eg bromine or iodine.

In process (b), $L_1$ is a leaving group such as halogen, eg chlorine.

In process (c), $L_2$ is a leaving group such as halogen, eg bromine.

In process (c), $L_3$ is a leaving group such as halogen, eg chlorine.

In process (e), $L_4$ is a leaving group such as halogen, eg bromine or iodine.

In process (f) L is a leaving group such as halogen, eg bromine or iodine.

Typical reaction conditions for process (a) comprise heating the reaction mixture in a microwave apparatus in a suitable solvent (for example 1-methyl-2-pyrrolidinone or toluene) in the presence of a coupling agent (such as Copper iodide), of a base (such as potassium carbonate or potassium hydroxide or potassium phosphate), and of a chelating agent (such as N,N'-dimethyl-1,2-cyclohexanediamine) at a temperature comprised between 130 and 200° C.

Typical reaction conditions for process (b) comprise stirring at room temperature in a suitable solvent (such as DCM), in the presence of a base (such as TEA or pyridine together with catalytic DMAP). Alternative reaction conditions for process (b) comprise heating in a microwave apparatus (for example ay 100° C. without any solvent.

Typical reaction conditions for process (c)-(step I) comprise stirring the mixture at room temperature in a dipolar solvent (such as DMF), in the presence of a base (for example potassium carbonate). Typical conditions for oxidation (step II) comprise reaction at room temperature with MCPBA in a suitable solvent (such as DCM), in the presence of $KHCO_3$.

Typical reaction conditions for process (d) comprise stirring the mixture at room temperature in a suitable solvent (such as DCM), in the presence of a base (such as TEA).

Typical reaction conditions for process (e) comprise reaction in a suitable solvent (such as DCM or DMF), in the presence of a base (for example 2,6-lutidine or potassium carbonate) at a temperature ranging from room temperature to 60° C.

Typical conditions for process (f)-(step I) comprise reaction at reflux in a suitable solvent (such as dioxane), in the presence of a base (such as DIPEA) and of a an appropriate catalyst (for example palladiumdibenzyliden acetone). Typical conditions for oxidation (step II) comprise reaction at room temperature with MCPBA in a suitable solvent (such as DCM).

In one aspect of the present invention, there is provided a synthetic process for the preparation of compounds of formula (IIa), i.e. compounds of formula (II) wherein P is hydrogen. This process comprises the following steps:

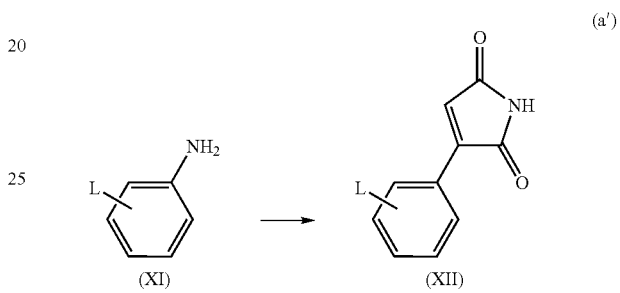

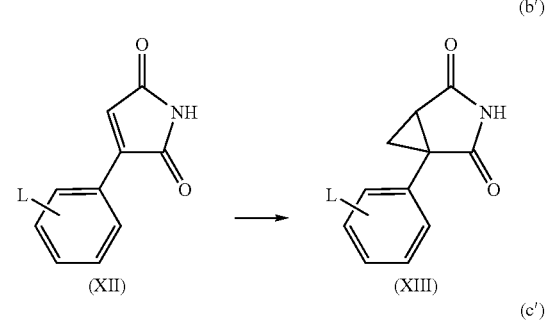

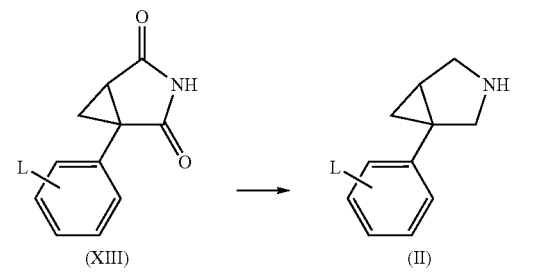

wherein:

L is a leaving group;

step (a') is diazotation of an aniline (XI) followed by reaction with maleimide to give 3-arylmaleimide (XII);

step (b') is cyclopropanation of (XII) to provide bicyclic imide (XIII); and step (c') means reduction of imide (XIII) to give compounds of formula (II).

Step (a') may be effected using conventional methods for the Meerwein reaction (e.g. *J. Am. Chem. Soc.* 1955, 77, 2313 describes the formation of arylmaleimides using this approach). Alternatively, in many cases this step is suitably performed applying a procedure where to a mixture of maleimide, an appropriate copper (II) salt such as anhydrous $CuCl_2$, and a suitable organonitrite, such as tert-butyl nitrite, in a compatible solvent, such as acetonitrile, is slowly added a solution of a compound of formula (XI). This is followed by allowing time to react as appropriate and a suitable workup.

Step (b') consists of slow addition of a solution of purified compound of formula (XII), or mixtures containing a compound of formula (XII), dissolved in a suitable solvent such as dimethylsulfoxide, to a solution of trimethylsulfoxonium iodide in a suitable solvent such as dimethylsulfoxide and a suitable base, such as sodium hydride. This is followed by allowing time to react as appropriate and a suitable workup.

Step (c') can be performed using a suitable reducing agent in a compatible solvent, such as borane in tetrahydrofuran or Red-Al® in toluene at an appropriate temperature, such as for example 65° C. in the case of borane as the reducing agent. This is followed by a suitable workup.

In another embodiment of the present invention, compounds of formula (IIb), i.e. compounds of formula (II) wherein P is not hydrogen, may be obtained starting from compounds of formula (IIa) through procedures well known in the art.

Compounds of formula (I) have been found to exhibit affinity for dopamine receptors, in particular the $D_3$ receptor, and are expected to be useful in the treatment of disease states which require modulation of such receptors, such as drug dependency or psychotic conditions. Such affinity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In the context of the present invention, pKi (corresponding to the antilogarithm of Ki) is used instead of Ki and the compounds of the present invention typically show pKi greater than 6.5. In one aspect the present invention provides compounds of formula (I) having a pKi comprised between 6.5 and 8. In another aspect the present invention provides compounds of formula (I) having a pKi comprised between 8 and 9. In a further aspect the present invention provides compounds of formula (I) having a pKi greater than 9.

Many of the compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. It has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of the present invention are provided which have higher (e.g. $\geq 10\times$ or $\geq 100\times$ higher) affinity for dopamine $D_3$ than dopamine $D_2$ receptors (such affinity can be measured using standard methodology for example using cloned dopamine receptors—see herein). Said compounds may suitably be used as selective modulators of $D_3$ receptors.

From the localisation of $D_3$ receptors, it could also be envisaged that the compounds could also have utility for the treatment of a substance-related disorder where it has been suggested that $D_3$ receptors are involved (e.g. see Levant, 1997, Pharmacol. Rev., 49, 231-252). Examples of such substance abuse include alcohol, cocaine, heroin and nicotine abuse. Compounds of formula (I) may be used for treatment of all aspects of drug dependency including drug intake, relapse to drug-seeking behaviour following abstinence and withdrawal symptoms from drugs of abuse such as alcohol, cocaine, opiates, nicotine, benzodiazepines and inhibition of tolerance induced by opioids. In addition, compounds of formula (I) and salts and solvates thereof may be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the development and maintenance of drug dependence.

The compounds of formula (I) are of potential use as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242). Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, eating disorders, sexual dysfunction, sleep disorders, emesis, movement disorders, obsessive-compulsive disorders, amnesia, aggression, autism, vertigo, dementia, circadian rhythm disorders and gastric motility disorders e.g. IBS.

A wide range of psychiatric and neuropsychiatric disorders appear to be related to Obsessive-Compulsive Disorder, and form a family of related disorders referred to as obsessive-compulsive (OC) spectrum disorders. The compounds of formula (I) may be used for the treatment of an obsessive-compulsive spectrum disorder, including somatoform disorders such as body dysmorphic disorder and hyperchondriasis, bulimia nervosa, anorexia nervosa, binge eating, paraphilia and nonparaphilic sexual addictions, Sydeham's chorea, torticollis, autism, compulsive hoarding, and movement disorders, including Tourette's syndrome. As used herein, the phrase "obsessive-compulsive spectrum disorder" is intended to include Obsessive-Compulsive Disorder.

The compounds of formula (I) are also useful for the treatment of premature ejaculation.

Within the context of the present invention, the terms describing the indications used herein are classified in the Diagnostic and Statistical Manual of Mental Disorders, 4th Edition, published by the American Psychiatric Association (DSM-IV) and/or the International Classification of Diseases, 10th Edition (ICD-10). The various subtypes of the disorders mentioned herein are contemplated as part of the present invention. Numbers in brackets after the listed diseases below refer to the classification code in DSM-IV.

Within the context of the present invention, the term "substance-related disorder" includes:—

Substance-related disorders including Substance Use Disorders such as Substance Dependence, Substance Craving and Substance Abuse; Substance-Induced Disorders such as Substance Intoxication, Substance Withdrawal, Substance-Induced Delirium, Substance-Induced Persisting Dementia, Substance-Induced Persisting Amnestic Disorder, Substance-Induced Psychotic Disorder, Substance-Induced Mood Disorder, Substance-Induced Anxiety Disorder, Substance-Induced Sexual Dysfunction, Substance-Induced Sleep Disorder and Hallucinogen Persisting Perception Disorder (Flashbacks); Alcohol-Related Disorders such as Alcohol Dependence (303.90), Alcohol Abuse (305.00), Alcohol Intoxication (303.00), Alcohol Withdrawal (291.81), Alcohol Intoxication Delirium, Alcohol Withdrawal Delirium, Alcohol-Induced Persisting Dementia, Alcohol-Induced Persisting Amnestic Disorder, Alcohol-Induced Psychotic Disorder, Alcohol-Induced Mood Disorder, Alcohol-Induced Anxiety Disorder, Alcohol-Induced Sexual Dysfunction, Alcohol-Induced Sleep Disorder and Alcohol-Related Disorder Not Otherwise Specified (291.9); Amphetamine (or Amphetamine-Like)-Related Disorders such as Amphetamine Dependence (304.40), Amphetamine Abuse (305.70), Amphetamine Intoxication (292.89), Amphetamine Withdrawal (292.0), Amphetamine Intoxication Delirium, Amphetamine Induced Psychotic Disorder, Amphetamine-Induced Mood Disorder, Amphetamine-Induced Anxiety Disorder, Amphetamine-Induced Sexual Dysfunction, Amphetamine-Induced Sleep Disorder and Amphetamine-Related Disorder Not Otherwise Specified (292.9); Caffeine Related Disorders such as Caffeine Intoxication (305.90), Caffeine-Induced Anxiety Disorder, Caffeine-Induced Sleep Disorder and Caffeine-Related Disorder Not Otherwise Specified (292.9); Cannabis-Related Disorders such as Cannabis Dependence (304.30), Cannabis Abuse (305.20), Cannabis Intoxication (292.89), Cannabis Intoxication Delirium, Cannabis-Induced Psychotic Disorder, Cannabis-Induced Anxiety Disorder and Cannabis-Related Disorder Not Otherwise Specified (292.9); Cocaine-Related Disorders such as Cocaine Dependence (304.20), Cocaine Abuse (305.60), Cocaine Intoxication (292.89), Cocaine Withdrawal (292.0), Cocaine Intoxication Delirium, Cocaine-Induced Psychotic Disorder, Cocaine-Induced Mood Disorder, Cocaine-Induced Anxiety Disorder, Cocaine-Induced Sexual Dysfunction, Cocaine-Induced Sleep Disorder and Cocaine-Related Disorder Not Otherwise Specified (292.9); Hallucinogen-Related Disorders such as Hallucinogen Dependence (304.50), Hallucinogen Abuse (305.30), Hallucinogen Intoxication (292.89), Hallucinogen Persisting Perception Disorder (Flashbacks) (292.89), Hallucinogen Intoxication Delirium, Hallucinogen-Induced Psychotic Disorder, Hallucinogen-Induced Mood Disorder, Hallucinogen-Induced Anxiety Disorder and Hallucinogen-Related Disorder Not Otherwise Specified (292.9); Inhalant-Related Disorders such as Inhalant Dependence (304.60), Inhalant Abuse (305.90), Inhalant Intoxication (292.89), Inhalant Intoxication Delirium, Inhalant-Induced Persisting Dementia, Inhalant-Induced Psychotic Disorder, Inhalant-Induced Mood Disorder, Inhalant-Induced Anxiety Disorder and Inhalant-Related Disorder Not Otherwise Specified (292.9); Nicotine-Related Disorders such as Nicotine Dependence (305.1), Nicotine Withdrawal (292.0) and Nicotine-Related Disorder Not Otherwise Specified (292.9); Opioid-Related Disorders such as Opioid Dependence (304.00), Opioid Abuse (305.50), Opioid Intoxication (292.89), Opioid Withdrawal (292.0), Opioid Intoxication Delirium, Opioid-Induced Psychotic Disorder, Opioid-Induced Mood Disorder, Opioid-Induced Sexual Dysfunction, Opioid-Induced Sleep Disorder and Opioid-Related Disorder Not Otherwise Specified (292.9); Phencyclidine (or Phencyclidine-Like)-Related Disorders such as Phencyclidine Dependence (304.60), Phencyclidine Abuse (305.90), Phencyclidine Intoxication (292.89), Phencyclidine Intoxication Delirium, Phencyclidine-Induced Psychotic Disorder, Phencyclidine-Induced Mood Disorder, Phencyclidine-Induced Anxiety Disorder and Phencyclidine-Related Disorder Not Otherwise Specified (292.9); Sedative-, Hypnotic-, or Anxiolytic-Related Disorders such as Sedative, Hypnotic, or Anxiolytic Dependence (304.10), Sedative, Hypnotic, or Anxiolytic Abuse (305.40), Sedative, Hypnotic, or Anxiolytic Intoxication (292.89), Sedative, Hypnotic, or Anxiolytic Withdrawal (292.0), Sedative, Hypnotic, or Anxiolytic Intoxication Delirium, Sedative, Hypnotic, or Anxiolytic Withdrawal Delirium, Sedative-, Hypnotic-, or Anxiolytic-Persisting Dementia, Sedative-, Hypnotic-, or Anxiolytic-Persisting Amnestic Disorder, Sedative-, Hypnotic-, or Anxiolytic-Induced Psychotic Disorder, Sedative-, Hypnotic-, or Anxiolytic-Induced Mood Disorder, Sedative-, Hypnotic-, or Anxiolytic-Induced Anxiety Disorder Sedative-, Hypnotic-, or Anxiolytic-Induced Sexual Dysfunction, Sedative-, Hypnotic-, or Anxiolytic-Induced Sleep Disorder and Sedative-, Hypnotic-, or Anxiolytic-Related Disorder Not Otherwise Specified (292.9); Polysubstance-Related Disorder such as Polysubstance Dependence (304.80); and Other (or Unknown) Substance-Related Disorders such as Anabolic Steroids, Nitrate Inhalants and Nitrous Oxide.

Within the context of the present invention, the term "psychotic disorder" includes:—

Schizophrenia including the subtypes Paranoid Type (295.30), Disorganised Type (295.10), Catatonic Type (295.20), Undifferentiated Type (295.90) and Residual Type (295.60); Schizophreniform Disorder (295.40); Schizoaffective Disorder (295.70) including the subtypes Bipolar Type and Depressive Type; Delusional Disorder (297.1) including the subtypes Erotomanic Type, Grandiose Type, Jealous Type, Persecutory Type, Somatic Type, Mixed Type and Unspecified Type; Brief Psychotic Disorder (298.8); Shared Psychotic Disorder (297.3); Psychotic Disorder Due to a General Medical Condition including the subtypes With Delusions and With Hallucinations; Substance-Induced Psychotic Disorder including the subtypes With Delusions (293.81) and With Hallucinations (293.82); and Psychotic Disorder Not Otherwise Specified (298.9).

In a further aspect therefore the present invention provides a method of treating a condition for which modulation [especially inhibition/antagonism (which may also translate into inverse agonism in constitutively active receptor systems)] of dopamine receptors (especially dopamine $D_3$ receptors) is beneficial, which comprises administering to a mammal (e.g. human) in need thereof an effective amount of a compound of formula (I) or a pharmaceutically (i.e physiologically) acceptable salt thereof. In one embodiment, the condition is a substance-related disorder, a psychotic disorder or an obsessive compulsive spectrum disorder.

The invention also provides the use of a compound of formula (I) or a salt thereof in the manufacture of a medicament for the treatment of a condition in a mammal for which modulation [especially inhibition/antagonism (which may also translate into inverse agonism in constitutively active receptor systems)] of dopamine receptors (especially dopamine $D_3$ receptors) is beneficial.

The invention also provides a compound of formula (I) or a salt thereof for use in the treatment of a condition in a mammal for which modulation [especially inhibition/antagonism (which may also translate into inverse agonism in constitutively active receptor systems)] of dopamine receptors (especially dopamine $D_3$ receptors) is beneficial.

In one embodiment, the compounds of the present invention are used in the treatment of a substance-related disorder, a psychotic disorder, an obsessive compulsive spectrum disorder or premature ejaculation.

Thus, a still further aspect the invention provides a method of treating a psychotic disorder (e.g. schizophrenia), a substance-related disorder or an obsessive compulsive spectrum disorder, which comprises administering to a mammal (e.g. human) in need thereof an effective amount of a compound of formula (I) as herein defined or a salt thereof.

Also provided is the use of a compound of formula (I) or a salt thereof in the manufacture of a medicament for the treatment of a a psychotic disorder (e.g. schizophrenia), a substance-related disorder, an obsessive compulsive spectrum disorder or premature ejaculation.

Also provided is a compound of formula (I) or a salt thereof for use in the treatment of a psychotic disorder (e.g. schizophrenia), a substance-related disorder, an obsessive compulsive spectrum disorder or premature ejaculation.

Also provided is a compound of formula (I) or a salt thereof for use as a therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I) or a pharmaceutically (i.e physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their salts which are active when given orally can be formulated as liquids or solids, for example syrups, suspensions or emulsions, tablets, capsules and lozenges.

A liquid formulation will generally consist of a suspension or solution of the compound or salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or salt in a sterile aqueous carrier or parenterally acceptable oil, for example polyethylene glycol, polyvinyl pyrrolidone, lecithin, arachis oil or sesame oil. Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluoro-chlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

Compositions for rectal administration are conveniently in the form of suppositories containing a conventional suppository base such as cocoa butter.

Compositions suitable for transdermal administration include ointments, gels and patches.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the formula (I) or a salt thereof calculated as the free base.

The pharmaceutically acceptable compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a salt thereof calculated as the free base, the compound being administered 1 to 4 times per day. Suitably the compounds will be administered for a period of continuous therapy, for example for a week or more.

Biological Test Methods

Functional potency and intrinsic activity of compounds of this invention can be measured by the following GTPγS scintillation proximity assay (GTPγS-SPA). Cells used in the study are Chinese Hamster Ovary (CHO) Cells.

Cell Line

CHO_D2

CHO_D3

Compounds may be tested according to two alternative protocols:

a) Cell membranes are prepared as follows. Cell pellets are resuspended in 10 volumes of 50 mM HEPES, 1 mM EDTA pH 7.4, using KOH. On the day the following proteases are added to the buffer just prior to giving the homogenisation buffer.

$2.12 \times 10^{-6}$M Leupeptin (Sigma L2884)–5000×stock=5 mg/ml in buffer 25 ug/ml Bacitracin (Sigma B0125)–1000×stock=25 mg/ml in buffer 1 mM PMSF–100×stock=17 mg/ml in 100% ethanol $2 \times 10^{-6}$M Pepstatin A–1000×stock=2 mM in 100% DMSO The cells are homogenised by 2×15 second bursts in a 1 litre Glass Waring blender in a class two biohazard cabinet. The resulting suspension is spun at 500 g for 20 mins (Beckman T21 centrifuge: 1550 rpm). The supernatant is withdrawn with a 25 ml pipette, aliquotted into pre-chilled centrifuge tubes and spun at 48,000 g to pellet membrane fragments (Beckman T1270: 23,000 rpm for 30 mins). The final 48,000 g pellet is resuspended in Homogenisation Buffer, (4× the volume of the original cell pellet). The 48,000 g pellet is resuspended by vortexing for 5 seconds and homogenized in a dounce homogenizer 10-15 stokes. The prep is distributed into appropriate sized aliquots, (200-1000 ul), in polypropylene tubes and store at −80° C. Protein content in the membrane preparations is evaluated with the Bradford protein assay.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 90 mins at 4° C.) membranes, 5 µg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 10 mM $MgCl_2$, 60 µg/ml saponin and 30 µM GDP is added. The third addition was a 20% TAV addition of either buffer, (agonist format) or $EC_{80}$ final assay concentration of agonist, Quinelorane, prepared in assay buffer (antagonist format). The assay was started by the addition of 29% TAV of GTPγ[$^{35}$S] 0.38 nM final (37 MBq/ml, 1160 Ci/mmol, Amersham). After all additions assay plates are spun down for 1 min at 1,000 rpm. Assay plates are counted on a Viewlux, 613/55 filter, for 5 min., between 2-6 hours after the final addition.

The effect of the test drug over the basal generates $EC_{50}$ value by an iterative least squares curve fitting programme, expressed in the table as $pEC_{50}$ (i.e. $-logEC_{50}$). The ratio between the maximal effect of the test drug and the maximal effect of full agonist, Quinelorane, generates the Intrinsic Activity (IA) value (i.e. IA=1 full agonist, IA<1 partial agonist). fpKi values of test drug are calculated from the $IC_{50}$ generated by "antagonist format" experiment, using Cheng & Prusoff equation: fKi=$IC_{50}$/1+([A]/$EC_{50}$) where: [A] is the concentration of the agonist 5-HT in the assay and $EC_{50}$ is the 5-HT $EC_{50}$ value obtained in the same experiment. fpki is defined as $-logfKi$.

b) Cell membranes are prepared as follows. Cell pellets are resuspended in 10 volumes of 50 mM HEPES, 1 mM EDTA pH 7.4, using KOH. On the day the following proteases are added to the buffer just prior to giving the homogenisation buffer.

$10^{-4}$M Leupeptin (Sigma L2884)

25 ug/ml Bacitracin (Sigma B0125)

1 mM PMSF–100× stock=17 mg/ml in 100% ethanol $2 \times 10^{-6}$M Pepstatin A–500×stock=1 mM in 100% ethanol The cells were homgenised within a glass waring blender for 2×15 secs in 200 mls of 50 mM HEPES+10-4M leupeptin+25 ug/ml bacitracin+1 mM EDTA+1 mM PMSF+2 uM Pepstatin A, (the latter 2 reagents added as fresh ×100 and ×500 stocks respectively in ethanol). The blender was plunged into ice for 5 mins after the first burst and 10-40 mins after the final burst to allow foam to dissipate. The material was then spun at 500 g for 20 mins and the supernatant spun for 36 mins at 48,000 g. The pellet was resuspended in the same buffer as above but without PMSF and Pepstatin A. The material was then forced through a 0.6 mm needle, made up to the required volume, (usually ×4 the volume of the original cell pellet), aliquoted and stored frozen at −80 deg C.

The final top concentration of test drug is 3 uM in the assay and 11 points serial dilution curves 1:4 in 100% DMSO are carried out using a Biomek FX. The test drug at 1% total assay volume (TAV) is added to a solid, white, 384 well assay plate. 50% TAV of precoupled (for 60 mins at RT) membranes, 5 µg/well, and Wheatgerm Agglutinin Polystyrene Scintillation Proximity Assay beads (RPNQ0260, Amersham), 0.25 mg/well, in 20 mM HEPES pH 7.4, 100 mM NaCl, 10 mM $MgCl_2$, 60 µg/ml saponin and 30 µM GDP is added. The third addition was a 20% TAV addition of either buffer, (agonist format) or EC80 final assay concentration of agonist, Quinelorane, prepared in assay buffer (antagonist format). The assay was started by the addition of 29% TAV of GTP [35S] 0.38 nM final (37 MBq/ml, 1160 Ci/mmol, Amersham). After all additions assay plates are spun down for 1 min at 1,000 rpm. Assay plates are counted on a Viewlux, 613/55 filter, for 5 min., between 3-6 hours after the final addition.

The effect of the test drug over the basal generates EC50 value by an iterative least squares curve fitting programme, expressed in the table as pEC50 (i.e. −logEC50). The ratio between the maximal effect of the test drug and the maximal effect of full agonist, Quinelorane, generates the Intrinsic Activity (IA) value (i.e. IA=1 full agonist, IA<1 partial agonist). fpKi values of test drug are calculated from the $IC_{50}$ generated by "antagonist format" experiment, using Cheng & Prusoff equation: fKi=IC50/1+([A]/EC50) where: [A] is the concentration of the agonist Quinelorane in the assay and EC50 is the Quinelorane EC50 value obtained in the same experiment. fpKi is defined as −logfki.

The compounds of the invention herein disclosed have pKi values within the range of 6.5-10.5 at the dopamine D3 receptor. In another embodiment, the compounds of the invention herein disclosed have pKi values within the range of 7.5-10.5 at the dopamine D3 receptor. In another embodiment, the compounds of the invention herein disclosed have pKi values within the range of 8.0-10.5 at the dopamine D3 receptor. pKi results are only estimated to be accurate to about ±0.3-0.5.

The compounds of the invention exemplified herein above have selectivity over D2 greater than 10. In another embodiment, the compounds of the invention exemplified herein above have selectivity over D2 greater than 20. In a further embodiment, the compounds of the invention exemplified herein above have selectivity over D2 greater than 30.

EXAMPLES

The invention is further illustrated by the following non-limiting examples.

All temperatures refer to ° C. Infrared spectra were measured on a FT-IR instrument. Compounds were analysed by direct infusion of the sample dissolved in acetonitrile into a mass spectra operated in positive electro spray (ES+) ionisation mode. Proton Magnetic Resonance ($^1$H-NMR) spectra were recorded at 400 MHz, chemical shifts are reported in ppm downfield (d) from Me₄Si, used as internal standard, and are assigned as singlets (s), broad singlets (bs), doublets (d), doublets of doublets (dd), triplets (t), quartets (q) or multiplets (m).

Column chromathography was carried out over silica gel (Merck AG Darmstaadt, Germany). The following abbreviations are used in the text: Vitride="Red-Al®", EtOAc=ethyl acetate, Et₂O=dietyl ether, DMF=N,N'-dimethylformamide, MeOH=methanol, TFA=trifluoroacetic acid, THF=tetrahydrofuran, TEA=triethylamine, EA=ethyl acetate; MCPBA=metachloroperbenzoic acid; DCM=dichloromethane; EtOH=ethanol; cy=cyclohexane; SCX=strong cation exchanger, Tlc refers to thin layer chromatography on silica plates, and dried refers to a solution dried over anhydrous sodium sulphate, r.t. (RT) refers to room temperature, Rt=retention time, DMSO=dimethyl sulfoxide; DIAD=diisopropyl azodicarboxylate.

Preparation 1:
3-(4-bromophenyl)-1H-pyrrole-2,5-dione (P1)

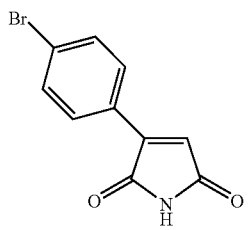

A solution of hydrochloric acid (37%, 27 mL) in water (11 mL) was added to 4-bromo aniline (15 g) at room temperature with vigorous stirring and the formed precipitate was allowed to stir for further 30 minutes. Temperature was reduced to 0° C. and a solution of sodium nitrite (6.60 g) in water (17 mL) was added dropwise to the stirred suspension. At the end of diazotisation, a clear yellow solution was obtained. Maleimide (16.90 g) in acetone (70 mL) was added dropwise at 0° C. and then the pH of the solution was adjusted to 3-3.5 by adding sodium acetate. Copper (II) chloride (1.76 g) was added to the vigorously stirred mixture. The reaction mixture was allowed to stir at 0° C. for 1 h and overnight at room temperature. Acetone was removed in vacuo, the residue was filtered and dried overnight in vacuo to give the crude title compound (14.12 g) which was used without further purification.

MS (m/z): 251 [M-H]⁻.

Preparation 2: (1R,5S/1S,5R)-1-(4-bromophenyl)-3-azabicyclo[3.1.0]hexane-2,4-dione (P2)

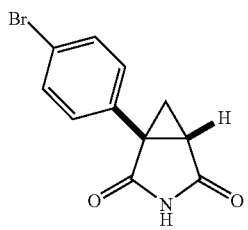

Milled potassium hydroxide (6.29 g) was added in small portions to a stirred solution of trimethylsulfoxonium iodide (24.66 g) in anhydrous DMSO (224 mL). The resulting mixture was allowed to stir at room temperature for 1.5 h then 3-(4-bromophenyl)-1H-pyrrole-2,5-dione (P1, 14.12 g) dissolved in DMSO (90 mL) was then added dropwise and the resulting mixture was allowed to stir at room temperature for 20 minutes. Reaction temperature was brought to 0° C. and aqueous saturated NH₄Cl (150 mL) was slowly added, followed by Et₂O (200 mL). After separation of the two phases, the aqueous layer was repeatedly extracted with Et₂O (3×100 mL). Combined organic layers were washed with brine and then dried over Na₂SO₄. Evaporation of the solvent gave the crude title compound (9.61 g) which was used without further purification.

MS (m/z): 265.1 [M-H]⁻.

Preparation 3: (1R,5S/1S,5R)-1-(4-bromophenyl)-3-azabicyclo[3.1.0]hexane (P3)

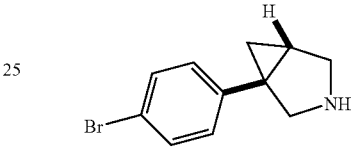

To stirred BH₃-THF complex in THF (1M, 145 mL) at 0° C. under N₂, a solution of (1R,5S/1S,5R)-1-(4-bromophenyl)-3-azabicyclo[3.1.0]hexane-2,4-dione (P2, 9.61 g) in 180 mL of dry tetrahydrofuran was slowly added. The reaction mixture was stirred at room temperature for 15 min and then warmed to reflux for 4 h then cooled to 0° C. and aqueous HCl (6N, 7.5 mL) was added cautiously and the reaction mixture stirred for 2 h. Solid NaOH was added up to pH~9, the reaction mixture was extracted twice with ether and the organic phase was washed with water, dried over Na₂SO₄ and evaporated under vacuum to give the crude title compound (8.5 g) which was used without further purification.

NMR (¹H, CDCl₃): δ 7.35 (d, 2H), 7.02 (d, 2H), 3.25-2.96 (m, 4H), 1.63 (dd, 1H), 1.55 (dd, 1H), 1.30 (dd, 1H), NH not observed. MS (m/z): 238.1 [MH]⁺.

Preparation 4: (1R,5S/1S,5R)-1,1-dimethylethyl-1-(4-bromophenyl)-3-azabicyclo[3.1.0]hexane-3-carboxylate (P4)

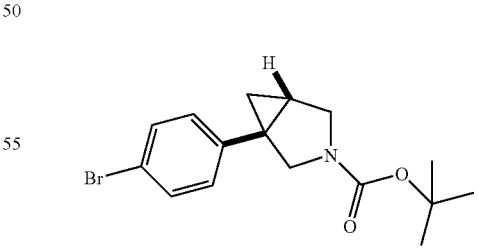

To a stirred solution of (1R,5S/1S,5R)-1-(4-bromophenyl)-3-azabicyclo[3.1.0]hexane (P3, 8.5 g) in dichloromethane (130 mL) at room temperature, triethylamine (6.5 mL) and bis(1,1-dimethylethyl) dicarbonate (8.6 g) were added. Stirring was continued for 6 h, then the reaction mixture was concentrated under vacuum and the crude product treated with diethyl ether and water. The organic phase was washed with saturated ammonium chloride solution, dried over sodium sulfate and the solvent evaporated under vacuum to give a crude product that was purified by chromatography over silica gel (cyclohexane/ETOAC 9/1) affording the title compound in 11.50 g yield.

MS (m/z): 282.1 [MH —C$_4$H$_8$]$^+$.

Preparation 5: (1R,5S/1S,5R)-1,1-dimethylethyl-1-(3-bromophenyl)-3-azabicyclo[3.1.0]hexane-3-carboxylate (P5)

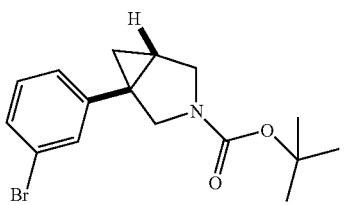

The title compound was prepared in analogy to the method described for Preparations 1-4 starting from 3-bromoaniline.

MS (m/z): 282.1 [MH —C$_4$H$_8$]$^+$.

Preparation 6: (1R,5S/1S,5R)-1,1-dimethylethyl-1-[3-(methyloxy)phenyl]-3-azabicyclo[3.1.0]hexane-3-carboxylate (P6)

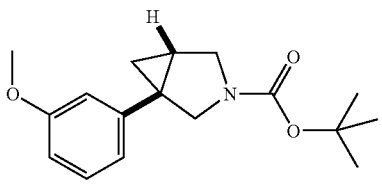

The title compound was prepared in analogy to the method described for Preparations 1-4 starting from 3-methoxyaniline.

MS (m/z): 233.1 [MH —C$_4$H$_8$]$^+$.

Preparation 7: (1R,5S/1S,5R)-1,1-dimethylethyl-1-(3-hydroxy-4-nitrophenyl)-3-azabicyclo[3.1.0]hexane-3-carboxylate (P7)

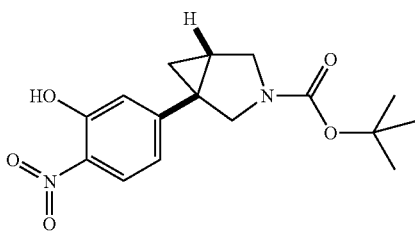

To a solution of (1R,5S/1S,5R)-1,1-dimethylethyl-1-[3-(methyloxy)phenyl]-3-azabicyclo[3.1.0]hexane-3-carboxylate (P6, 1.81 g) in dichloromethane was added dropwise at −78° C. a BBr$_3$ in dichloromethane (1M, 19.1 mL). After 3 h at 25° C. the mixture was cooled at 0° C. and aqueous Na$_2$CO$_3$ (2M, 38.3 mL) was added dropwise with stirring. After 10 min the dichloromethane was evaporated in vacuo, tetrahydrofuran (72 mL) and bis(1,1-dimethylethyl) dicarbonate (4.18 g) were added and the mixture vigorously stirred for 14 h. Most tetrahydrofuran was removed by evaporation in vacuo, the residue brought to pH=6 by adding aqueous HCl (2M), diluted with water and extracted with EtOAc. The organic layer was washed with brine, dried (Na2SO4), filtered and volatiles removed in vacuo. From this material were obtained, following column chromatography, 1.33 g of a yellow solidifying gum.

To material thus obtained (1.55 g) in dichloromethane (15 mL) containing silica gel 60 (5 g), with cooling in a cold bath at 0° C., nitric acid (70%, 0.36 mL) was added dropwise over 10 min with vigorous stirring. After 10 min additional nitric acid (70%, 0.036 mL) was added. After additional 5 min the mixture was filtered and the solids washed with EtOAc. The resulting solution was concentrated and submitted to column chromatography (Cy/EtOAc 1:1) to provide the title compound as a faint yellow solid (0.47 g).

NMR ($^1$H, CDCl$_3$): δ 10.65 (br s, 1H), 8.01 (d, 1H), 6.88 (d, 1H), 6.68 (d, 1H), 4.02 (m, 1H), 3.77 (m, 1H), 3.65 (m, 1H), 3.53 (m, 1H), 1.99 (m, 1H), 1.50 (s, 9H), 1.20 (m, 1H), 1.05 (m, 1H). MS (m/z): 319 [M-H]$^−$.

Preparation 8: (1S,5R/1R,5S)-1,1-dimethylethyl-1-[4-amino-3-(methyloxy)phenyl]-3-azabicyclo[3.1.0]hexane-3-carboxylate (P8)

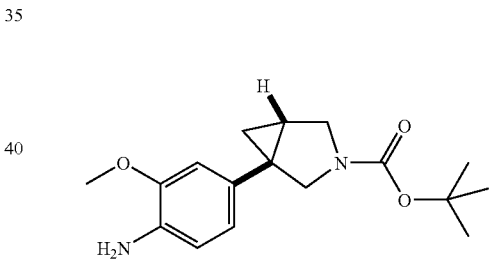

(1R,5S/1S,5R)-1,1-dimethylethyl-1-(3-hydroxy-4-nitrophenyl)-3-azabicyclo[3.1.0]hexane-3-carboxylate (P7, 0.47 g) was allowed to react with iodomethane (0.14 mL) in N,N-dimethylformamide (4 mL) in the presence of potassium carbonate (0.41 g) with stirring. After 7 h water was added, the mixture kept for 14 h prior to partitioning between water and EtOAc:cyclohexane 2:1. The organic phase was washed (brine) and concentrated in vacuo to give a brown oil (0.52 g). The material thus obtained (0.52 g) was hydrogenated with vigorous stirring at atmospheric pressure and 25° C. for 4 h in the presence of palladium (10%) on activated carbon (0.1 g) in EtOH (10 mL) and EtOAc (10 mL). Filtration, washing the solids with EtOAc, followed by evaporation of volatiles from the resulting solution in vacuo gave the title compound as a grey solid (0.46 g).

NMR ($^1$H, CDCl$_3$): δ 6.6-6.7 (m, 3H), 3.35-3.97 (multiple m, 7H), ca. 1.5-4 (vbr, 2H), 1.70 (bs, 1H), 1.46 (s, 9H), 1.07 (bm, 1H), 0.77 (bm, 1H).

Preparation 9: (1S,5R/1R,5S)-1,1-dimethylethyl-1-(4-iodophenyl)-3-azabicyclo[3.1.0]hexane-3-carboxylate (P9)

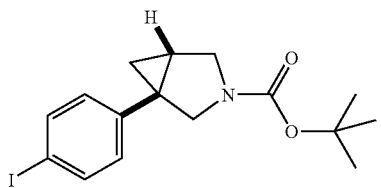

The title compound was prepared in analogy to the method described for Preparations 1-4 starting from 4-iodoaniline.
MS (m/z): 329 [MH —$C_4H_8$]+.

Preparation 10: 1,1-Dimethylethyl (1S,5R/1R,5S)-1-[4-(hydroxymethyl)phenyl]-3-azabicyclo[3.1.0]hexane-3-carboxylate (P10)

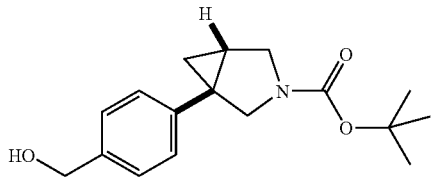

To a stirred solution of 1,1-dimethylethyl (1S,5R/1R,5S)-1-(4-iodophenyl)-3-azabicyclo[3.1.0]hexane-3-carboxylate (P9, 1.2 g) in tetrahydrofuran (10 mL) was added slowly via syringe at −13° C. isopropylmagnesium chloride (2 M in tetrahydrofuran, 3.1 mL). The light brown solution was kept for 1 h at which time it had reached −10° C. N,N-dimethylformamide (0.6 mL) was added and the mixture was allowed to warm to 25° C. over 3 h. Water (10 mL) and aqueous HCl (2 M, 4.6 mL) were carefully added and vacuum was briefly applied to evaporate highly volatile components. Sodium borohydride (0.12 g) and methanol (30 mL) were added with stirring. After 90 min HOAc (3.6 mL) was carefully added, the mixture partitioned between water and $Et_2O$, the organic layer consecutively washed with aqueous $NaHCO_3$ and brine, volatiles evaporated and the residue submitted to column chromatography to give the title compound (Cy/EtOAc 20:80) (0.51 g) as a slowly solidifying colourless oil.
NMR ($^1$H, $CDCl_3$): δ 7.32 (d, 2H), 7.20 (br d, 2H), 4.70 (s, 2H), 3.90-4.02 (m, 1H), 3.50-3.78 (m, 3H), 1.81 (m, 1H), 1.68 (br s, 1H), 1.49 (s, 9H), 1.10 (m, 1H), 0.88 (m, 1H). MS (m/z): 233 [MH —$C_4H_8$]+.

Preparation 11: 1,1-dimethylethyl (1S,5R/1R,5S)-1-[4-(bromomethyl)phenyl]-3-azabicyclo[3.1.0]hexane-3-carboxylate (P11)

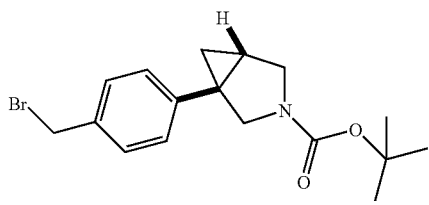

To a stirred solution of 1,1-dimethylethyl (1S,5R/1R,5S)-1-[4-(hydroxymethyl)phenyl]-3-azabicyclo[3.1.0]hexane-3-carboxylate (P10, 181 mg) and triphenylphosphine (166 mg) in 6 mL of dry dichloromethane, carbon tetrabromide (210 mg) was added. After 1 h at room temperature, water was added (6 mL) and the organic layer was extracted with DCM, washed with saturated aqueous NaCl and dried over $Na_2SO_4$. The solution was filtered and the filtrate was concentrated in vacuo. The crude was purified by column chromatography (cycloexane:EtAc=100 to 5) to give the title compound as an oil (130 mg).
MS (m/z): 296 [MH —$C_4H_8$]+.

Preparation 12: 4-(1-methylethyl)benzenesulfonamide (P12)

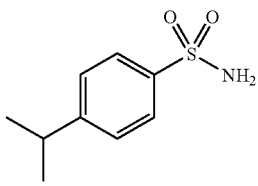

To concentrated aqueous ammonia (1.75 mL) in tetrahydrofuran (50 mL) at 0° C. with stirring was added over 2 min via syringe 4-(1-methylethyl)benzenesulfonyl chloride (3.3 g). A white precipitate was observed. Additional concentrated aqueous ammonia (1.75 mL) was added after 5 min. After 4 h volatiles were evaporated and the residue partitioned between EtOAc and aqueous $NaHCO_3$. The organic layer was washed with brine, dried ($Na_2SO_4$) and volatiles evaporated to give the title crude compound as a colourless powder that was used without further purification.
NMR ($^1$H, $CDCl_3$): δ 7.83 (d, 2H), 7.35 (d, 2H), 4.8 (bs, 2H), 2.95 (sept, 1H), 1.25 (d, 6H).

Preparation 13: 4-(1,1-dimethylpropyl)benzenesulfonamide (P13)

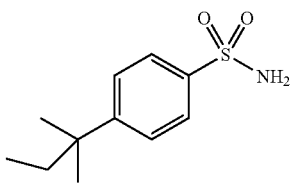

The title compound was prepared in 80% yield as described in preparation 12 starting from 4-(1,1-dimethylpropyl)benzenesulfonyl chloride (70 mg).
MS (m/z): 228 [MH]+.

Preparation 14: 1,1-dimethylethyl (1S,5R/1R,5S) 1-(4-aminophenyl)-3-azabicyclo[3.1.0]hexane-3-carboxylate (P14)

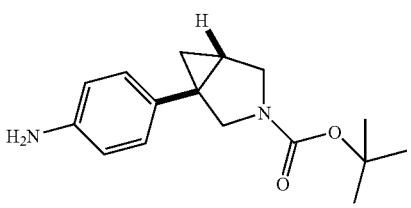

To a stirred solution of (1R,5S/1S,5R)-1,1-dimethylethyl-1-(4-bromophenyl)-3-azabicyclo[3.1.0]hexane-3-carboxylate (P4, 570 mg) in dry toluene (20 mL), litium bis(trimethylsilyl)amide (0.276 mL of a 1M solution in THF) was added. Then, 15 mg of tributhylphosphine and 44 mg of tris(dibenzylidenacetone)dipalladium(0) was added and the reaction mixture stirred at room temperature for 5 h. 20 mL of a 2M solution of hydrochloric acid was added and the resulting mixture stirred for additional 30 min, then treated with water and extracted with DCM. The organic phase was washed with water, dried over Na2SO4 and evaporated under reduced pressure. The crude product was purified by flash chromatography (eluting with cyclohexane/ethylacetate 90:10) to give the title compound (220 mg).
MS (m/z): 275 [MH]+.

Preparation 15: (1S,5R/1R,5S)-1-(4-bromophenyl)-3-(3-fluoropropyl)-3-azabicyclo[3.1.0]hexane (P15)

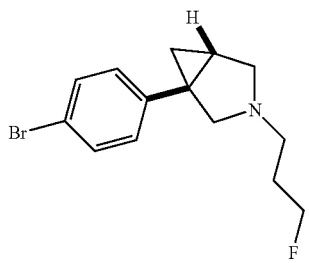

To a stirred solution of (1R,5S/1S,5R)-1-(4-bromophenyl)-3-azabicyclo[3.1.0]hexane (P3, 570 mg) in dry DMF (2.5 mL), 1-bromo-3-fluoropropane (70 mg), potassium carbonate (100 mg) and a catalytic amount of KI were added and the reaction mixture stirred at 60 C for 1.5 h. The crude was loaded on SCX column eluting with MeOH/NH3 to obtained the title compound (120 mg).
MS (m/z): 297 [MH]+.

Preparation 16: 1,1-dimethylethyl (1R,5S/1S,5R)-1-[4-({[4-(1-methylethyl)phenyl]methyl}thio)phenyl]-3-azabicyclo[3.1.0]hexane-3-carboxylate (P16)

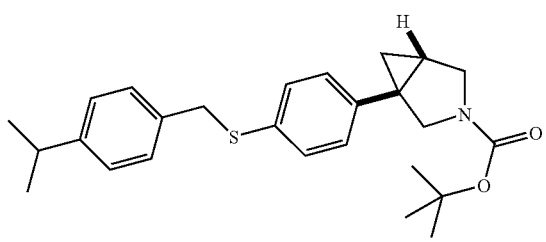

To a solution of 1,1-dimethylethyl (1S,5R/1R,5S)-1-(4-bromophenyl)-3-azabicyclo[3.1.0]hexane-3-carboxylate (P4, 200 mg) and [4-(1-methylethyl)phenyl]methanethiol (148 mg) in dry dioxane (7 mL) palladiumdibenzyliden acetone (14 mg) and dry diisopropylethylamine (153 mg) were added. Mixture was refluxed for 2 days, solvent evaporated and the crude purified by chromatography eluting with cyclohexane to obtain 200 mg of the title compound as yellow oil.
MS (m/z): 423 [MH]+.

Preparation 17: 1,1-dimethylethyl (1R,5S/1S,5R)-1-[4-({[4-(1-methylethyl)phenyl]methyl}sulfonyl)phenyl]-3-azabicyclo[3.1.0]hexane-3-carboxylate (P17)

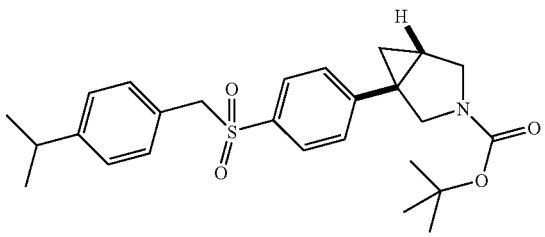

To a solution of 50 mg of 1,1-dimethylethyl (1R,5S/1S,5R)-1-[4-({[4-(1-methylethyl)phenyl]methyl}thio)phenyl]-3-azabicyclo[3.1.0]hexane-3-carboxylate (P16) in dry dichloromethane (2 mL), was added 2.5 eq of MCPBA dissolved in 2 mL of dry dichloromethane. The mixture was stirred at room temperature for 1 h and then 2.5 eq of MCPBA dissolved in 2 mL of dry was added. After 1 h, the solvent was evaporated and the crude purified by silica chromatography (Cy/EA 100/0-50:50) to obtain 38 mg of the title compound.
MS (m/z): 454 [MH]+.

Example 1

N-{4-[(1S,5R/1R,5S)-3-azabicyclo[3.1.0]hex-1-yl]phenyl}-4-(1-methylethyl)benzenesulfonamide hydrochloride (E1)

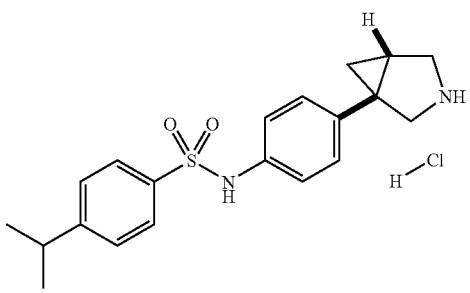

To a solution of 1,1-dimethylethyl (1S,5R/1R,5S)-1-(4-bromophenyl)-3-azabicyclo[3.1.0]hexane-3-carboxylate (P4, 50 mg) and 4-(1-methylethyl)benzenesulfonamide (65 mg) in N-methylpirrolidinone (0.5 mL) in a vial were added potassium carbonate (41 mg) and copper iodide (3 mg). The vial was sealed and heated by microwave at 195° C. for 2.5 h. The reaction mixture was cooled to room temperature, filtered through a SCX cartridge (eluting with methanol then with 2N NH4OH in methanol). The filtrate was concentrated in vacuo and the crude product was purified by flash chromatography (eluting with dichloromethane/methanol 96:4) to give 35 mg of N-{4-[(1S,5R/1R,5S)-3-azabicyclo[3.1.0]hex-1-yl]phenyl}-4-(1-methylethyl)benzenesulfonamide. To a solution of this material in dichloromethane (1 mL) was added HCl (98 μL, 1M in Et2O), the solvent evaporated under vacuum and the material thus obtained triturated with Et2O to give 36 mg of the title compound as a white slightly hygroscopic solid.

NMR ($^1$H, CD$_3$OD): δ 7.68 (d, 2H), 7.35 (d, 2H), 7.18 (d, 2H), 7.10 (d, 2H), 3.94 (d, 1H), 3.76 (d, 1H), 3.54 (m, 2H), 2.97 (s, 3H), 2.94 (m, 1H), 2.11 (m, 1H), 1.21 (m, 8H). MS (m/z): 371 [MH]$^+$.

Example 1 was submitted to semi-preparative HPLC to give the separated enantiomers, by using a chiral column chiralpak AD-H 5 um, 250×21 mm, eluent A: n-hexane; B: Ethanol+0.1% isopropylamine, gradient isocratic 40% B, flow rate 6 mL/min, detection UV at 254 nm. Retention times given were obtained using an analytical HPLC using a chiral column chiralpak AD-H 5 um, 250×4.6 mm, eluent A: n-hexane; B: ethanol+0.1% isopropylamine, gradient isocratic 40% B, flow rate 0.8 mL/min, detection UV at 200-400 nm.

Example 1A (E1A—Enantiomer 1, N-{4-[(1S,5R or 1R,5S)-3-azabicyclo[3.1.0]hex-1-yl]phenyl}-4-(1-methylethyl)benzenesulfonamide hydrochloride) was recovered as a white solid. Rt.=15.99 min.

Example 1B (E1B—Enantiomer 2, N-{4-[(1R,5R or 1S,5R)-3-azabicyclo[3.1.0]hex-1-yl]phenyl}-4-(1-methylethyl)benzenesulfonamide hydrochloride) was recovered as a white solid. Rt.=18.73 min.

Hydrochloride salts of Enantiomer 1 and 2 were prepared following the procedure described for Example 1.

Enantiomer 2 showed fpki (D3)>1 log-unit higher than Enantiomer 1.

Example 2

4-(1-methylethyl)-N-{4-[(1S,5R/1R,5S)-3-(2-propen-1-yl)-3-azabicyclo[3.1.0]hex-1-yl]phenyl}benzenesulfonamide hydrochloride (E2)

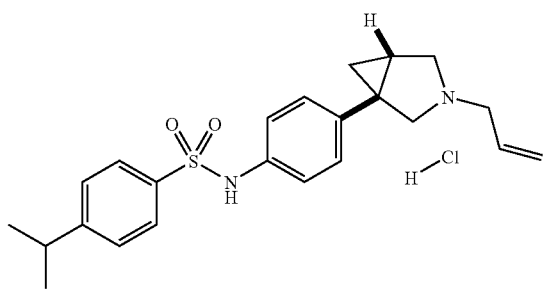

To a stirred solution of N-{4-[(1R,5S/1S,5R)-3-azabicyclo[3.1.0]hex-1-yl]phenyl}-4-(1-methylethyl)benzenesulfonamide (31 mg) in DCM (0.5 mL), at room temperature, lutidine (13 μL) and allyl bromide (8 μL) were added and the stirring continued for 4 h. The reaction mixture was treated with water and extracted with DCM, the organic phase was washed with water, dried over Na2SO4 and evaporated under reduced pressure. The crude product was purified by flash chromatography (eluting with DCM/methanol 96:4) to give the free base of the title compound (8 mg).

This product was dissolved in dichloromethane (2 ml), and hydrochloridric acid was added dropwise (0.072 ml, 1M/ether), at room temperature. Following solvent evaporation gave the title compound (3 mg) as a yellow solid.

NMR ($^1$H, CD$_3$OD): δ 7.68 (d, 2H), 7.29 (d, 2H), 7.02 (d, 2H), 6.98 (d, 2H), 6.53 (b, 1H), 5.89 (m, 1H), 5.2 (d, 1H), 5.11 (bd, 1H), 3.31 (b, 1H), 3.16 (bs, 2H), 3.12 (b, 1H), 2.94 (m, 1H), 2.54 (b, 2H), 1.66 (s, 1H), 1.46 (b, 1H), 1.24 (d, 6H), 0.76 (bs, 1H).

MS (m/z): 397 [MH]$^+$.

Example 3

N-{4-[(1S,5R/1R,5S)-3-Ethyl-3-azabicyclo[3.1.0]hex-1-yl]phenyl}-4-(1-methylethyl)benzenesulfonamide hydrochloride (E3)

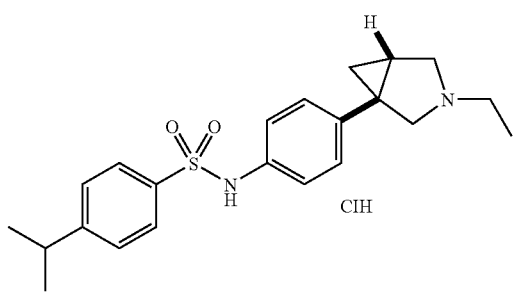

N-[4-(3-Azabicyclo[3.1.0]hex-1-yl)phenyl]-4-(1-methylethyl)benzenesulfonamide (21 mg) was allowed to react with stirring with iodoethane (0.006 mL) in dry dichloromethane (1 mL) in the presence of 2,6-lutidine (0.008 mL). After 18 h the resulting brown mixture was partitioned between dichloromethane and aqueous (ca. 0.5 M) Na$_2$CO$_3$. The dichloromethane layer was collected, concentrated and submitted to column chromatography. The free base of the title compound thus obtained was converted into the hydrochloride salt by dissolving it in dichloromethane, adding excess HCl (1 M in Et$_2$O), evaporating volatiles in vacuo, and triturating the residue with Et$_2$O:EtOAc 1:1 (ca. 0.1 mL/mg). The title compound was obtained as a brown solid (7 mg).

NMR ($^1$H, CD$_3$OD): δ 7.68 (d, 2H), 7.34 (d, 2H), 7.18 (d, 2H), 7.10 (d, 2H), 3.97 (d, 1H), 3.77 (d, 1H), 3.54 (dd, 1H), 3.50 (d, 1H), 3.28 (m, 2H), 2.92 (m, 1H), 2.10 (m, 1H), 1.35 (t, 3H), 1.21 (m, 8H). MS (m/z): 385 [MH]$^+$.

Example 4

N-{4-[(1S,5R/1R,5S)-3-Methyl-3-azabicyclo[3.1.0]hex-1-yl]phenyl}-4-(1-methylethyl)benzenesulfonamide hydrochloride (E4)

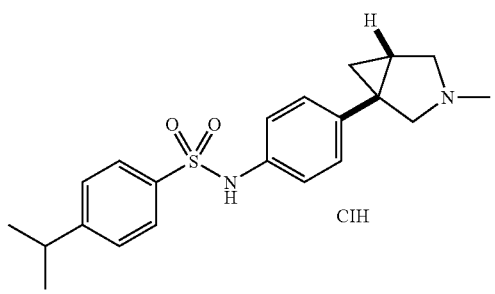

N-[4-(3-Azabicyclo[3.1.0]hex-1-yl)phenyl]-4-(1-methylethyl)benzenesulfonamide (118 mg) was allowed to react with stirring with iodomethane (0.025 mL) in dry dichloromethane (3 mL) in the presence of 2,6-lutidine (0.046 mL). A precipitate formed after 1 h. After 18 h the resulting brown mixture was partitioned between dichloromethane and aqueous (ca. 0.5 M) Na$_2$CO$_3$. The dichloromethane layer was collected, concentrated and submitted to column chromatography. The free base of the title compound thus obtained was converted into the hydrochloride salt by dissolving it in dichloromethane, adding excess HCl (1 M in Et$_2$O), evaporating volatiles in vacuo, and triturating the residue with Et$_2$O: EtOAc 1:1 (ca. 0.1 mL/mg). The title compound was obtained as an off-white solid (49 mg).

NMR ($^1$H, CD$_3$OD): δ 7.68 (d, 2H), 7.35 (d, 2H), 7.18 (d, 2H), 7.10 (d, 2H), 3.94 (d, 1H), 3.76 (d, 1H), 3.54 (m, 2H), 2.97 (s, 3H), 2.94 (m, 1H), 2.11 (m, 1H), 1.21 (m, 8H). MS (m/z): 371 [MH]$^+$.

Example 5

N-{3-[(1S,5R/1R,5S))-3-methyl-3-azabicyclo[3.1.0]hex-1-yl]phenyl}-4-(1-methylethyl)benzenesulfonamide hydrochloride (E5)

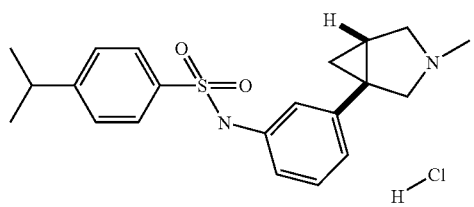

To a solution of (1R,5S/1S,5R)-1,1-dimethylethyl-1-(3-bromophenyl)-3-azabicyclo[3.1.0]hexane-3-carboxylate (P5, 0.20 g) and 4-(1-methylethyl)benzenesulfonamide (0.26 g) in N-methylpirrolidinone (2 mL) in a vial were added potassium carbonate (0.16 g) and copper iodide (12 mg). The vial was sealed and heated by microwave at 195° C. for 2.5 h. The reaction mixture was cooled to room temperature, filtered through a SCX cartridge (eluting with methanol then with 2N NH$_4$OH in methanol). The filtrate was concentrated in vacuo and the crude product was purified by flash chromatography (eluting with dichloromethane/methanol 96:4) to give 85 mg of N-{3-[(1R,5S/1S,5R)-3-azabicyclo[3.1.0]hex-1-yl]phenyl}-4-(1-methylethyl)benzenesulfonamide. To a stirred solution of this material (37 mg) in DCM (1 mL) at RT, formaldehyde (0.016 mL, soluz. 37% water) was added followed after 15 min by sodium triacetoxyborohydride (50 mg). The reaction mixture was stirred for 3 h, after which time aqueous saturated potassium carbonate was added and the mixture was extracted with ethyl acetate. The organic phase was concentrated in vacuo and the crude product was purified by flash chromatography (eluting with dichloromethane/methanol 96:4) to give 11 mg of the free base of the title compound. To a solution of this material in dichloromethane (0.5 mL) was added HCl (30 µL, 1M in Et$_2$O), the solvent evaporated under vacuum and the material thus obtained triturated with Et$_2$O to give 11 mg of the title compound as a white slightly hygroscopic solid.

NMR ($^1$H, CD$_3$OD): δ 10.27 (bs, 2H), 7.68 (d, 2H), 7.42 (d, 2H), 7.18 (t, 1H), 6.92 (m, 3H), 3.84 (m, 1H), 3.61 (m, 1H), 3.44 (m, 2H), 2.93 (m, 1H), 2.82 (s, 3H), 2.02 (m, 1H), 1.49 (t, 1H), 1.17 (d, 6H), 0.92 (t, 1H). MS (m/z): 371 [MH]$^+$.

Example 6

N-{4-[(1S,5R/1R,5S)-3-azabicyclo[3.1.0]hex-1-yl]phenyl}-N-methyl-4-(1-methylethyl)benzenesulfonamide hydrochloride (E6)

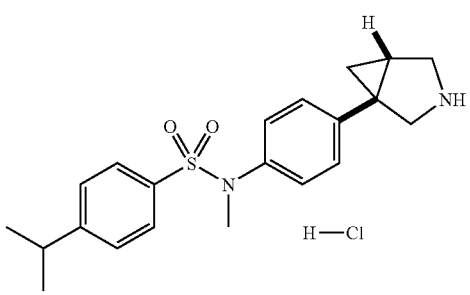

A mixture of (1S,5R/1R,5S)-1,1-dimethylethyl-1-(4-iodophenyl)-3-azabicyclo[3.1.0]hexane-3-carboxylate (P9, 50 mg), 4-(1-methylethyl)benzenesulfonamide (33 mg), copper iodide (12 mg), (1R,2R)-diaminomethylcyclehexane diamine (4 mg) and potassium hydroxide (15 mg) in toluene (0.5 mL), was warmed in microwave at 130° C. After 1 h, additional copper iodide (50 mg) and (1R,2R)-diaminomethylcyclehexane diamine (100 mg) was added, and the mixture was warmed for an hour. The solvent was evaporated under vacuum, the crude product was dissolved in DCM and the solution washed with saturated aqueous NH$_4$Cl, dried over Na$_2$SO$_4$ and concentrated under vacuum. The crude product was purified by flash chromatography (eluting with DCM/MeOH 99:1) to give 45 mg of (1S,5R/1R,5S)-1,1-dimethylethyl-1-[4-({[4-(1-methylethyl)phenyl]sulfonyl}amino)phenyl]-3-azabicyclo[3.1.0]hexane-3-carboxylate. To a stirred solution of this intermediate (45 mg), triphenylphosphine (52 mg), MeOH (0.15 mL) in toluene (0.5 mL) at 0° C., DIAD (35 mg, 40% in toluene) was added over 20 minutes. The refrigerant bath was removed and stirring was continued for an additional hour. Volatiles were evaporated in vacuo, the crude dissolved in DCM, the organic phase washed with aqueous saturated NaHCO$_3$, dried over Na$_2$SO$_4$ and concentrated under reduced pressure. The crude was purified by flash chromatography (eluting with cycloexane/ethyl acetate 95:5) to give 24 mg of 1,1-dimethylethyl (1R,5S)-1-[4-(methyl{[4-(1-methylethyl)phenyl]sulfonyl}amino)phenyl]-3-azabicyclo[3.1.0]hexane-3-carboxylate. This product was dissolved in DCM (1 mL) and TFA (1 mL) was added. After 1 h, the reaction mixture was poured in ice/NaHCO$_3$, extracted whit DCM, the organic phase evaporated in vacuo, and the crude product was filtered through a SCX cartridge (eluting with methanol then with 2N NH$_4$OH in methanol). The filtrate was concentrated in vacuo to give 9 mg of the free base of the title compound. To a solution of this material in DCM (0.2 mL), HCl (0.024 mL, 1M in Et$_2$O) was added, the solvent evaporated under vacuum and the material thus obtained triturated with Et$_2$O to give 9 mg of the title compound as a white slightly hygroscopic solid.

NMR (¹H, CDCl₃): δ 7.49 (d, 2H), 7.42 (d, 2H), 7.26 (d, 2H), 7.1 (d, 2H), 3.7 (d, 1H), 3.58 (m, 2H), 3.46 (d, 1H), 3.17 (s, 3H), 3.1 (m, 1H), 2.15 (m, 1H), 1.32 (d, 6H), 1.1 (m, 1H). MS (m/z): 371 [MH]⁺.

Example 7

N-[4-[(1S,5R/1R,5S)-3-Azabicyclo[3.1.0]hex-1-yl]-2-(methyloxy)phenyl]-4-(1-methylethyl)benzenesulfonamide hydrochloride (E7)

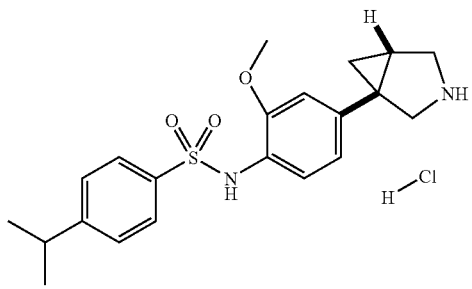

1,1-Dimethylethyl (1S,5R/1R,5S)-1-[4-amino-3-(methyloxy)phenyl]-3-azabicyclo[3.1.0]hexane-3-carboxylate (P8, 0.071 g) was allowed to react with 4-(1-methylethyl)benzenesulfonyl chloride (77 mg) in dichloromethane in the presence of pyridine (0.057 mL) and N,N-dimethyl-4-pyridinamine (6 mg) for 4 h. Water (1 mL) was added and the mixture stirred for 30 min, then partitioned between water and dichloromethane. The organic layer was collected, concentrated and submitted to column chromatography. Products were treated with trifluoroacetic acid (1 mL) in dichloromethane (2 mL) for 3 h, volatiles evaporated and the residues converted to the hydrochloride salts as described for Example 1 [triturating the title compound using Et₂O EtOAc 2:1] to give the title compound as an off-white solid (30 mg).

NMR (¹H, CD₃OD): δ 7.63 (d, 2H), 7.40 (d, 1H), 7.32 (d, 2H), 6.85 (dd, 1H), 6.76 (d, 1H), 3.72 (dd, 1H), 3.64 (dd, 1H), 3.56 (m, 4H), 3.48 (dd, 1H), 2.94 (m, 1H), 2.13 (m, 1H), 1.33 (m, 1H), 1.24 (d, 6H), 1.06 (m, 1H). MS (m/z): 387 [MH]⁺.

Example 8

(1S,5R/1R,5S)-1-[4-({[4-(1-Methylethyl)phenyl]sulfonyl}methyl)phenyl]-3-azabicyclo[3.1.0]hexane hydrochloride (E8)

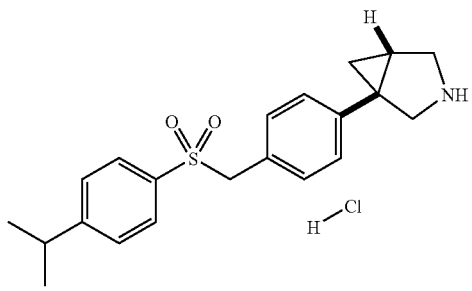

1,1-Dimethylethyl (1S,5R/1R,5S)-1-[4-(bromomethyl)phenyl]-3-azabicyclo[3.1.0]hexane-3-carboxylate (P11, 26 mg) in N,N-dimethylformamide (0.5 mL) was treated with 4-(1-methylethyl)benzenethiol (0.018 uL) and potassium carbonate (10 mg) with stirring for 16 h. Volatiles were evaporated in vacuo and the residue submitted to column chromatography. The thioether intermediate thus obtained (23 mg colourless film) was allowed to react with metachloroperbenzoic acid (37 mg, ≦77% titre) in dichloromethane (2 mL) in the presence of KHCO₃ (11 mg). After 1 h excess Na₂S₂O₃, NaHCO₃ (5% in water) and dichloromethane were added with vigorous stirring. The dichloromethane layer was collected, concentrated and the residue submitted to column chromatography. The material thus obtained was treated with trifluoroacetic acid (1 mL) in dichloromethane (2 mL) for 3 h, volatiles evaporated and the residues converted to the hydrochloride salts as described for Example 1 to give the title compound as a colourless solid (19 mg).

NMR (¹H, CD₃OD): δ 7.62 (d, 2H), 7.43 (d, 2H), 7.23 (d, 2H), 7.17 (d, 2H), 4.46 (s, 2H), 3.76 (d, 1H), 3.67 (dd, 1H), 3.61 (d, 1H), 3.52 (d, 1H), 3.00 (m, 1H), 2.17 (m, 1H), 1.28 (d, 6H), 1.26 (m, 1H), 1.12 (dd, 1H). MS (m/z): 356 [MH]⁺.

Example 9

N-{4-[(1S,5R/1R,5S)-3-Azabicyclo[3.1.0]hex-1-yl]phenyl}-4-(trifluoromethyl)benzenesulfonamide hydrochloride (E9)

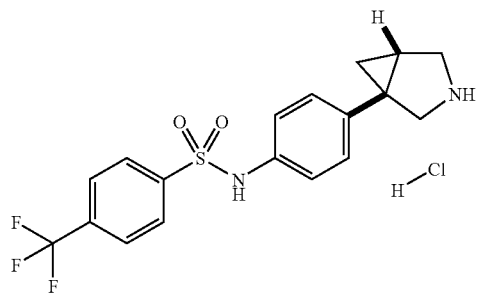

To a solution of (1S,5R/1R,5S)-1-(4-bromophenyl)-3-azabicyclo[3.1.0]hexane (P3, 0.10 g) and 4-(trifluoromethyl)benzenesulfonamide (0.10 g) in N-methylpyrrolidinone (1 mL) were added potassium carbonate (0.123 g) and CuI (15 mg). The mixture was heated in a sealed vessel using a microwave reactor at 200° C. for 1 h followed by two intervals of 50 min each at 195° C. Water was added and the mixture was extrated three times with dichloromethane, applied to an SCX cartridge, eluting with methanol then with 2N NH₄OH in methanol. Product containing fractions were concentrated in vacuo and purified by consecutive silica gel and NH2 silica (Biotage, product eluted in EtOAc:acetone gradient) chromatography. The free base of the title compound thus obtained was converted into the hydrochloride salt by dissolving it in dichloromethane, adding excess HCl (1 M in Et₂O), evaporating volatiles in vacuo, and triturating the residue with Et₂O:EtOAc 1:1 (ca. 0.1 mL/mg). The title compound was obtained as an orange solid (19 mg).

NMR (¹H, CD₃OD): δ 7.93 (d, 2H), 7.82 (d, 2H), 7.20 (d, 2H), 7.11 (d, 2H), 3.68 (d, 1H), 3.62 (d, 1H), 3.55 (d, 1H), 3.47 (m, 1H), 2.10 (m, 1H), 1.21 (m, 1H), 1.05 (m, 1H). MS (m/z): 383 [MH]⁺.

Example 10

N-{4-[(1S,5R/1R,5S)-3-azabicyclo[3.1.0]hex-1-yl]phenyl}-4-iodobenzenesulfonamide hydrochloride (E10)

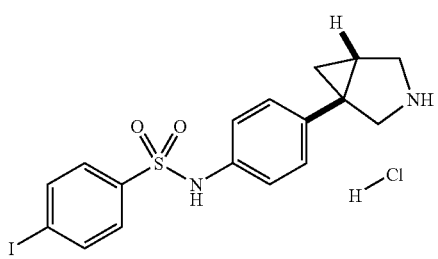

A mixture of 1,1-dimethylethyl(1R,5S)-1-(4-aminophenyl)-3-azabicyclo[3.1.0]hexane-3-carboxylate (P14, 150 mg) and 4-iodo-benzenesulfonylchloride (100 mg) was heated in a sealed vessel using a microwave reactor at 100° C. for 30 min. Water was added and the mixture was extracted with DCM, and then purified by silica flash cromatography The free base of the title compound thus obtained was converted into the hydrochloride salt by dissolving it in dichloromethane, adding excess HCl (1 M in Et$_2$O), evaporating volatiles in vacuo, and triturating the residue with Et$_2$O:EtOAc 1:1 (ca. 0.1 mL/mg). The title compound was obtained as solid (13 mg).

NMR ($^1$H, CD$_3$OD): δ ppm 0.95 (t, 1H) 1.10 (t, 1H) 1.91-2.07 (m, 1H) 3.38 (d, 1H) 3.44 (d, 1H) 3.52 (dd, 1H) 3.59 (d, 1H) 6.99 (d, 2H) 7.09 (d, 2H) 7.38 (d, 2H) 7.75 (d, 2H). MS (m/z): 439 [MH]$^+$.

Example 11

N-{4-[(1S,5R/1R,5S)-3-azabicyclo[3.1.0]hex-1-yl]phenyl}-4-butylbenzenesulfonamide hydrochloride (E11)

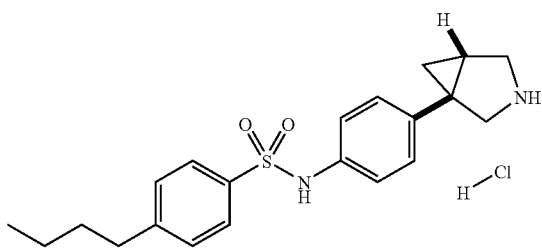

A mixture of 1,1-dimethylethyl(1R,5S)-1-(4-aminophenyl)-3-azabicyclo[3.1.0]hexane-3-carboxylate (P14, 20 mg) and 4-buthylbenzenesulfonylchloride (11 mg), dry TEA (0.02 mL) in DCM, was stirred at room temperature for 1 h. Solvent was evaporated and the crude purified by silica flash chromatography eluting with cyclohexane/ethylacetate 95/5. The N-terbutoxycarbonyl derivative of the title compound thus obtained was treated with trifluoracetic acid (0.5 ml) at room temperature for 1 h. Evaporation of the solvent and purification of the crude by SCX column gave the title compound as free base. The compound was then converted into the hydrochloride salt by dissolving it in dichloromethane, adding excess HCl (1 M in Et$_2$O), evaporating volatiles in vacuo, and triturating the residue with Et$_2$O:EtOAc 1:1 (ca. 0.1 mL/mg). The title compound was obtained as solid (5 mg).

NMR ($^1$H, CD$_3$OD): δ ppm 0.83 (t, 3H) 0.92-0.98 (m, 1H) 1.06-1.14 (m, 1H) 1.18-1.28 (m, 2H) 1.43-1.55 (m, 2H) 1.94-2.02 (m, 1H) 2.56 (t, 2H) 3.35-3.62 (m, 4H) 7.00 (d, 2H) 7.07 (d, 2H) 7.20 (d, 2H) 7.57 (d, 2H). MS (m/z): 369 [MH]$^+$.

Example 12

N-{4-[(1S,5R/1R,5S)-3-azabicyclo[3.1.0]hex-1-yl]phenyl}-4-(1,1-dimethylpropyl)benzenesulfonamide hydrochloride (E12)

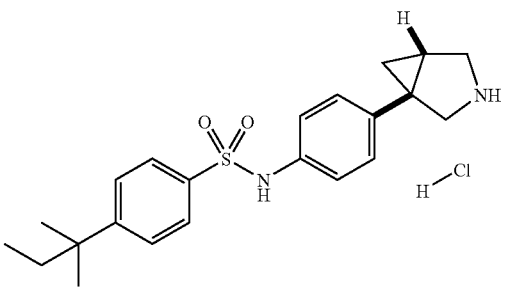

To a solution of (1S,5R/1R,5S)-1,1-dimethylethyl-1-(4-iodophenyl)-3-azabicyclo[3.1.0]hexane-3-carboxylate (P9, 0.53 g) and 4-(1,1-dimethylpropyl)benzenesulfonamide (P13, 0.4 g) in dry toluene copper iodide (11 mg), (1R,2R)-diaminomethylcyclehexane diamine (5 mg) and potassium hydroxide (16 mg) were added and the mixture warmed in microwave at 150° C. for 2 h. The solvent was evaporated under vacuum, the crude product was dissolved in DCM and the solution washed with saturated aqueous NH$_4$Cl, dried over Na$_2$SO$_4$ and concentrated under vacuum. The crude product was purified by flash chromatography (eluting with cyclohexane/ethylacetate 8/2) to give 11 mg of 1,1-dimethylethyl (1R,5S)-1-[4-({[4-(1,1-dimethylpropyl)phenyl]sulfonyl}amino)phenyl]-3-azabicyclo[3.1.0]hexane-3-carboxylate. To a stirred solution of this intermediate (11 mg) in DCM (1 mL), trifluoroacetic acid (0.5 ml) was added and the mixture stirred at room temperature for 1 h. Volatiles were evaporated in vacuo, the crude was purified by SCX cartridge (eluting with methanol then with 2N NH$_4$OH in methanol). The filtrate was concentrated in vacuo to give 10.5 mg of the free base of the title compound. The compound was then converted into the hydrochloride salt by dissolving it in dichloromethane, adding excess HCl (1 M in Et$_2$O), evaporating volatiles in vacuo, and triturating the residue with Et$_2$O:EtOAc 1:1 (ca. 0.1 mL/mg). The title compound was obtained as a white solid (11 mg).

NMR ($^1$H, CD$_3$OD): δ ppm 0.59 (t, 3H) 0.98-1.07 (m, 1H) 1.14-1.22 (m, 1H) 1.65 (q, 2H) 2.02-2.11 (m, 1H) 3.42-3.48 (m, 1H) 3.51 (d, 1H) 3.59 (dd, 1H) 3.65 (d, 1H) 7.06-7.11 (m, 1H) 7.14-7.19 (m, 1H) 7.42-7.49 (m, 1H) 7.65-7.72 (m, 1H) MS (m/z): 435 [MH]$^+$.

Example 13

N-{4-[(1S,5R/1R,5S)-3-azabicyclo[3.1.0]hex-1-yl]phenyl}-4-[(trifluoromethyl)oxy]benzenesulfonamide hydrochloride (E13)

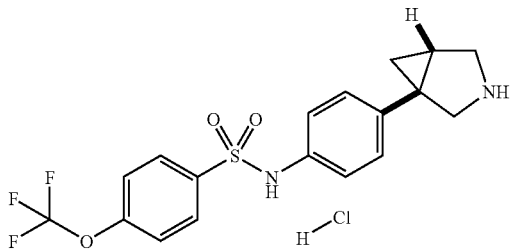

To a solution of (1S,5R/1R,5S)-1,1-dimethylethyl-1-(4-iodophenyl)-3-azabicyclo[3.1.0]hexane-3-carboxylate (P9, 0.53 g) and 4-[(trifluoromethyl)oxy]benzenesulfonamide (0.47 g) in dry toluene copper iodide (48 mg), (1R,2R)-diaminomethylcyclohexane diamine (70 mg) and potassium phosphate (55 mg) were added and the mixture warmed in microwave at 150° C. for 1 h. The solvent was evaporated under vacuum, the crude product was dissolved in DCM and the solution washed with saturated aqueous NH$_4$Cl, dried over Na$_2$SO$_4$ and concentrated under vacuum. The crude product was purified by flash chromatography (eluting with DCM/MeOH 9/1) to give 20 mg of 1,1-dimethylethyl (1R,5S)-1-{4-[({4-[(trifluoromethyl)oxy]phenyl}sulfonyl)amino]phenyl}-3-azabicyclo[3.1.0]hexane-3-carboxylate. To a stirred solution of this intermediate (18 mg) in DCM (1 mL), trifluoroacetic acid (0.5 ml) was added and the mixture stirred at room temperature for 1 h. Volatiles were evaporated in vacuo, the crude was purified by SCX cartridge (eluting with methanol then with 2N NH$_4$OH in methanol). The filtrate was concentrated in vacuo to give 10 mg of the free base of the title compound. The compound was then converted into the hydrochloride salt by dissolving it in dichloromethane, adding excess HCl (1 M in Et$_2$O), evaporating volatiles in vacuo, and triturating the residue with Et$_2$O:EtOAc 1:1 (ca. 0.1 mL/mg). The title compound was obtained as a white solid (10 mg).

MS (m/z): 397 [MH]$^+$.

Example 14

N-{4(1S,5R/1R,5S)-)-3-(3-fluoropropyl)-3-azabicyclo[3.1.0]hex-1-yl]phenyl}-4-(1-methylethyl)benzenesulfonamide hydrochloride (E14)

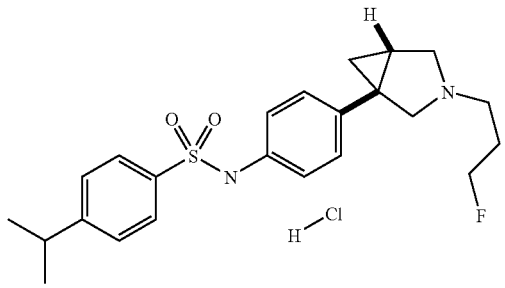

To a solution of (1S,5R/1R,5S)-1-(4-bromophenyl)-3-(3-fluoropropyl)-3-azabicyclo[3.1.0]hexane (P15, 50 mg) and 4-(1-methylethyl)benzenesulfonamide (67 mg) in toluene (1 mL) in a vial were added N,N'-dimethylcyclohexyamine (95 mg), copper iodide (64 mg), and KOH (19 mg). The vial was sealed and heated by microwave at 195° C. for 2.5 h. The reaction mixture was cooled to room temperature, filtered through a SCX cartridge (eluting with methanol then with 2N NH$_4$OH in methanol). The filtrate was concentrated in vacuo and the crude product was purified by flash chromatography (eluting with dichloromethane/methanol 96:4) to give 35 mg the title compound as a free base. To a solution of this material in dichloromethane (1 mL) was added HCl (98 μL, 1M in Et$_2$O), the solvent evaporated under vacuum and the material thus obtained triturated with Et$_2$O to give 36 mg of the title compound as a white slightly hygroscopic solid.

NMR ($^1$H, CD$_3$OD): δ ppm 1.07-1.19 (m, 1H) 1.21-1.28 (m, 1H) 1.24 (d, 6H) 2.01-2.10 (m, 2H) 2.08-2.15 (m, 1H) 2.90-3.01 (m, 1H) 3.24 (t, 2H) 3.33-3.49 (m, 1H) 3.56-3.72 (m, 1H) 3.76-3.96 (m, 1H) 4.50 (t, 1H) 4.53-4.62 (m, 1H) 4.59 (t, 1H) 7.10 (d, 2H) 7.16 (d, 2H) 7.37 (d, 2H) 7.69 (d, 2H) 8.27 (br. s., 1H)

MS (m/z): 417 [MH]$^+$.

Example 15

(1R,5S/1S,5R)-1-[4-({[4-(1-methylethyl)phenyl]methyl}sulfonyl)phenyl]-3-azabicyclo[3.1.0]hexane (E15)

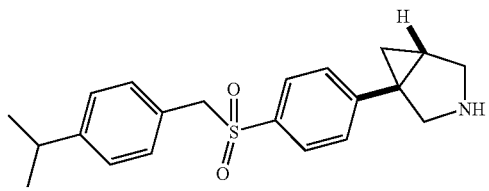

To a solution of 20 mg of 1,1-dimethylethyl 1,1-dimethylethyl (1R,5S/1S,5R)-1-[4-({[4-(1-methylethyl)phenyl]methyl}sulfonyl)phenyl]-3-azabicyclo[3.1.0]hexane-3-carboxylate (P17) in dry dichloromethane (2 mL), trifluoroacetic acid was added (1 mL) and the mixture stirred at room temperature for 1 h. The mixture was then loaded on SCX cartridge room temperature, filtered (eluting with methanol then with 2N NH$_4$OH in methanol). The filtrate was concentrated in vacuo to obtained 10 mg of the title compound.

MS (m/z): 354 [MH]$^+$.

Example 16

(1R,5S/1S,5R)-1-[4-({[4-(1-methylethyl)phenyl]methyl}sulfonyl)phenyl]-3-azabicyclo[3.1.0]hexane hydrochloride (E16)

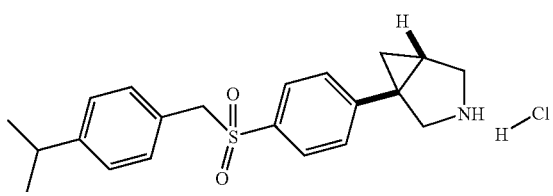

To a solution of 17.5 mg of 1,1-dimethylethyl (1R,5S/1S,5R)-1-[4-({[4-(1-methylethyl)phenyl]methyl}sulfonyl)phenyl]-3-azabicyclo[3.1.0]hexane-3-carboxylate (P17) in dry dichloromethane (1 mL), trifluoroacetic acid (1 mL) was added. After 1 h at room temperature, the crude was loaded on SCX cartridge room temperature, filtered (eluting with methanol then with 2N $NH_4OH$ in methanol). The filtrate was concentrated in vacuo and the obtained product was dissolved in dry dichloromethane (1 mL) and HCl was added (50 μL, 1M in $Et_2O$). The solvent evaporated under vacuum and the material thus obtained triturated with $Et_2O$ to give 10 mg of the title compound.

NMR (DMSO-$d_6$) δ ppm 1.18 (d, 6H) 1.16-1.23 (m, 1H) 1.39 (t, 1H) 2.24-2.34 (m, 1H) 2.79-2.91 (m, 1H) 3.34-3.45 (m, 1H) 3.42-3.63 (m, 2H) 3.69-3.80 (m, 1H) 4.60 (s, 2H) 6.99-7.30 (m, 4H) 7.45 (d, 2H) 7.69 (d, 2H) 9.14 (br. s., 1H) 9.54 (br. s., 1H)

Example 17

(1R,5S/1S,5R)-3-(3-fluoropropyl)-1-[4-({[4-(1-methylethyl)phenyl]methyl}sulfonyl)phenyl]-3-azabicyclo[3.1.0]hexane hydrochloride (E17)

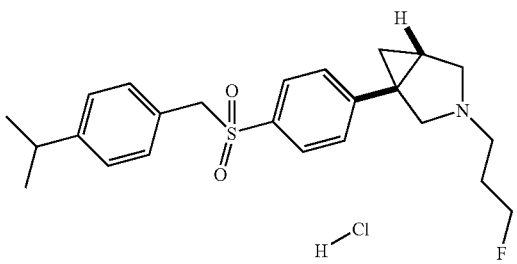

To a solution of 15.5 mg of (1R,5S/1S,5R)-1-[4-({[4-(1-methylethyl)phenyl]methyl}sulfonyl)phenyl]-3-azabicyclo[3.1.0]hexane in dry DMF (2 mL), 3-fluoropropylbromide (6 mg), $K_2CO_3$ (14 mg) and a catalytic amount of KI were added. The mixture was stirred at 60 C for 2 h, then cooled to room temperature, filtered through a SCX cartridge (eluting with methanol then with 2N $NH_4OH$ in methanol). The filtrate was concentrated in vacuo and the crude product was purified by flash chromatography (eluting with dichloromethane/methanol 96:4) to give 8 mg the title compound as a free base. To a solution of this material in dry dichloromethane (1 mL), HCl was added (50 μL, 1M in $Et_2O$). The solvent evaporated under vacuum and the material thus obtained triturated with $Et_2O$ to give 8 mg of the title compound.

NMR ($^1$H, $CD_3OD$): δ ppm 1.12 (d, 6H) 1.20-1.37 (m, 2H) 1.96-2.16 (m, 2H) 2.22-2.33 (m, 1H) 2.70-2.83 (m, 1H) 3.26-3.45 (m, 2H) 3.47-3.60 (m, 1H) 3.56-3.71 (m, 1H) 3.77 (d, 1H) 4.05 (d, 1H) 4.36 (s, 2H) 4.43 (t, 1H) 4.52 (t, 1H) 6.95 (d, 2H) 7.04 (d, 2H) 7.34 (d, 2H) 7.56 (d, 2H)

All publications, including but not limited to patents and patent applications, cited in this specification are herein incorporated by reference as if each individual publication were specifically and individually indicated to be incorporated by reference herein as though fully set forth.

The invention claimed is:
1. A compound of formula (IA) or a salt thereof:

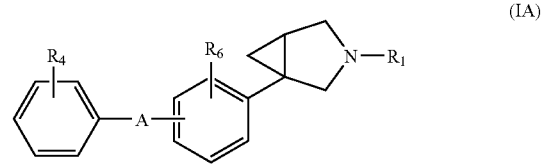

wherein:
A is attached to the phenyl group at the meta position or the para position relative to the cyclopropyl group, and is selected from the group consisting of —$SO_2NR_5$—, —$SO_2CR_2R_3$—, —$CR_2R_3SO_2$— and —$NR_5SO_2$—;

$R_1$ is hydrogen, $C_{1-6}$alkyl, halo$C_{1-6}$alkyl or $C_{2-6}$alkylene;

$R_2$ and $R_3$ are independently hydrogen or $C_{1-6}$alkyl;

$R_4$ is hydrogen, halogen, $C_{1-6}$alkyl, halo$C_{1-6}$alkyl, $C_{1-6}$alkoxy or halo$C_{1-6}$alkoxy;

$R_5$ is hydrogen, $C_{1-6}$alkyl, or a phenyl optionally substituted by $R_4$; and $R_6$ is hydrogen, $C_{1-6}$alkyl, halo$C_{1-6}$alkyl, $C_{1-6}$alkoxy or halo$C_{1-6}$alkoxy.

2. A compound as claimed in claim 1, wherein $R_4$ is $C_{1-6}$alkyl, halo$C_{1-6}$alkyl or halogen.

3. A compound as claimed in claim 1, wherein A is —$SO_2NR_5$— wherein $R_5$ is hydrogen, or A is —$SO_2CR_2R_3$— wherein $R_2$ and $R_3$ are hydrogen.

4. A compound as claimed in claim 1, wherein A is —$CR_2R_3SO_2$—wherein $R_2$ and $R_3$ are hydrogen.

5. A compound as claimed in claim 1, which is
N-{4-[(1S,5R/1R,5S)-3-azabicyclo[3.1.0]hex-1-yl]phenyl}-4-(1-methylethyl)benzenesulfonamide;
N-{4-[(1R,5S or 1S,5R)-3-azabicyclo[3.1.0]hex-1-yl]phenyl}-4-(1-methylethyl)benzenesulfonamide);
4-(1-methylethyl)-N-{4-[(1S,5R/1R,5S)-3-(2-propen-1-yl)-3-azabicyclo[3.1.0]hex-1-yl]phenyl}benzenesulfonamide;
N-{4-[(1S,5R/1R,5S)-3-Ethyl-3-azabicyclo[3.1.0]hex-1-yl]phenyl}-4-(1-methylethyl)benzenesulfonamide;
N-{4-[(1S,5R/1R,5S)-3-Methyl-3-azabicyclo[3.1.0]hex-1-yl]phenyl}-4-(1-methylethyl)benzenesulfonamide;
N-{3-[(1S,5R/1R,55S))-3-methyl-3-azabicyclo[3.1.0]hex-1-yl]phenyl}-4-(1-methylethyl)benzenesulfonamide;
N-{4-[(1S,5R/1R,5S)-3-azabicyclo[3.1.0]hex-1-yl]phenyl}-N-methyl-4-(1-methylethyl)benzenesulfonamide;
N-[4-[(1S,5R,1R,5S)-3-Azabicyclo[3.1.0]hex-1-yl]-2-(methyloxy)phenyl]-4-(1-methylethyl)benzenesulfonamide;
(1S,5R/1R,5S)-1-[4-({[4-(1-Methylethyl)phenyl]sulfonyl}methyl)phenyl]-3-azabicyclo[3.1.0]hexane;
N-{4-[(1S,5R/1R,5S)-3-Azabicyclo [3.1.0]hex-1-yl]phenyl}-4-(trifluoromethyl)benzenesulfonamide;
N-{4-[(1S,5R/1R,5S)-3-azabicyclo[3.1.0]hex-1-yl]phenyl}-4-iodobenzenesulfonamide;
N-{4-[(1S,5R/1R,5S)-3-azabicyclo[3.1.0]hex-1-yl]phenyl}-4-butylbenzenesulfonamide;
N-{4-[(1S,5R/1R,5S)-3-azabicyclo[3.1.0]hex-1-yl]phenyl}-4-(1,1-dimethylpropyl)benzenesulfonamide;
N-{4-[(1S,5R/1R,5S)-3-azabicyclo[3.1.0]hex-1-yl]phenyl}-4-[(trifluoromethyl)oxy]benzenesulfonamide;

N-{4(1S,5R/1R,5S)-3-(3-fluoropropyl)-3-azabicyclo [3.1.0]hex-1-yl]phenyl}-4-(1-methylethyl)benzene-sulfonamide;

(1R,5S/1S,5R)-1-[4-({[4-(1-methylethyl)phenyl] methyl}sulfonyl)phenyl]-3-azabicyclo[3.1.0]hexane;

(1R,5S/1S,5R)-3-(3-fluoropropyl)-1-[4-({[4-(1-methyl-ethyl)phenyl]methyl}sulfonyl)phenyl]-3-azabicyclo [3.1.0]hexane;

or a salt thereof.

6. A compound as claimed in claim 1, having a formula (IA)' or a salt thereof

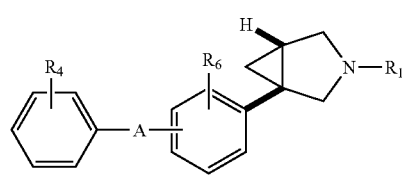

(I)' wherein $R_4$, $R_1$ and A are defined in claim 1 for compounds of formula (IA).

7. A process for preparing a compound as defined in claim, the process comprising:

(a) reacting a compound of formula (II):

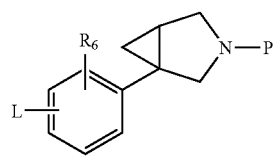

(II)

wherein P may be a suitable protecting group or a substituent $R_1$ as defined for formula (I) and L is a leaving group, with a compound of formula (III):

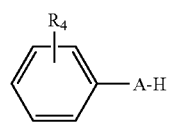

(III)

wherein $R_4$ and A are as defined for formula (I); or (b) for a compound of formula (Ia), i.e. a compound of formula (I) wherein A is —SO$_2$NH—, reacting a compound of formula (IV):

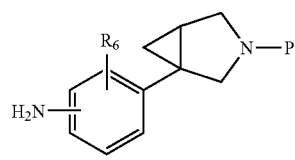

(IV)

wherein P may be a suitable protecting group or a substituent $R_1$ as defined for formula (I) and $R_6$ is as defined for formula (I) with a compound of formula (V):

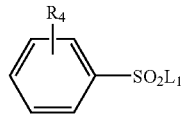

(V)

wherein $R_4$ is as defined for formula (I) and $L_1$ is a leaving group; or (c) for a compound of formula (Ib), i.e. a compound of formula (I) wherein A is —SO$_2$CR$_2$R$_3$—, reacting a compound of formula (VI):

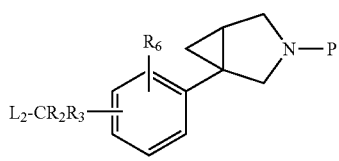

(VI)

wherein P may be a suitable protecting group or a substituent $R_1$ as defined for formula (I), $R_2$, $R_3$, and $R_6$ are as defined for formula (I) and $L_2$ is a leaving group, with a compound of formula (VII) (step I):

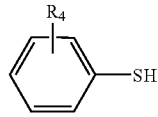

(VII)

wherein $R_4$ is as defined for formula (I), followed by an oxidation step for the sulphur atom (step II);

(d) for a compound of formula (Ic), i.e. a compound of formula (I) wherein A is —NR$_5$SO$_2$—, reacting a compound of formula (VIII):

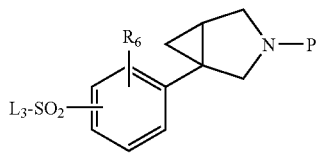

(VIII)

wherein P may be a suitable protecting group or a substituent $R_1$ as defined for formula (I) and $R_6$ is as defined for formula (I) and $L_3$ is a leaving group, with a compound of formula (IX):

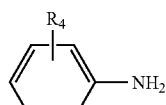

(IX)

wherein $R_4$ is as defined for formula (I);

(e) for a compound of formula (Id), i.e. a compound of formula (I) wherein $R_1$ is not hydrogen, reacting a compound of formula (Ie), i.e. a compound of formula (I) wherein $R_1$ is hydrogen:

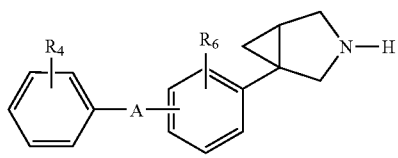
(Id)

with a compound $R_1L_4$ of formula, wherein R1 is as defined for formula (I) and $L_4$ is a leaving group;

(f) for a compound of formula (Ie), i.e. a compound of formula (I) wherein A is $-CR_2R_3SO_2-$, reacting a compound of formula (II):

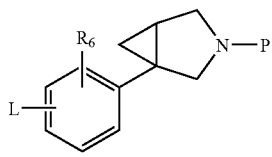
(II)

as above defined, with a compound of formula (X) (step I):

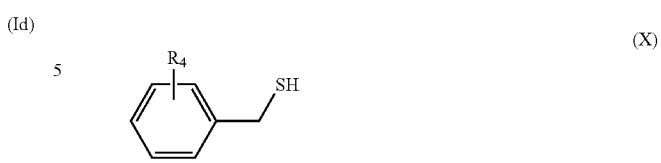
(X)

wherein $R_4$ is as defined for formula (I), followed by an oxidation step for the sulphur atom (step II);

and thereafter optionally for process (a), (b), (c), (d), (e) or (f):
   (i) removing any protecting group(s); and/or
   (ii) forming a salt; and/or
   (iii) converting a compound of formula (I) or a salt thereof to another compound of formula (I) or a salt thereof.

8. A pharmaceutical composition comprising a compound as claimed in claim 1 and a pharmaceutically acceptable carrier.

9. A method of treating a condition for which modulation of dopamine $D_3$ receptors is beneficial, which comprises administering to a mammal (e.g. human) in need thereof an effective amount of a compound of claim 1.

10. A method as claimed in claim 9, wherein the condition is a substance-related disorder is schizophrenia or premature ejaculation.

* * * * *